US012685635B2

(12) United States Patent
Schwarcz et al.

(10) Patent No.: US 12,685,635 B2
(45) Date of Patent: Jul. 21, 2026

(54) DELIVERY APPARATUS FOR MECHANICALLY EXPANDABLE VALVE

(71) Applicant: EDWARDS LIFESCIENCES CORPORATION, Irvine, CA (US)

(72) Inventors: Elazar Levi Schwarcz, Netanya (IL); Oren Cohen, Kadima (IL); Eitan Atias, Netanya (IL)

(73) Assignee: Edwards Lifesciences Corporation, Irvine, CA (US)

( * ) Notice: Subject to any disclaimer, the term of this patent is extended or adjusted under 35 U.S.C. 154(b) by 525 days.

(21) Appl. No.: 18/125,087

(22) Filed: Mar. 22, 2023

(65) Prior Publication Data
US 2023/0225863 A1      Jul. 20, 2023

Related U.S. Application Data

(63) Continuation of application No. PCT/US2021/052745, filed on Sep. 30, 2021.

(60) Provisional application No. 63/085,947, filed on Sep. 30, 2020.

(51) Int. Cl.
*A61F 2/24* (2006.01)
*A61F 2/95* (2013.01)

(52) U.S. Cl.
CPC ............ *A61F 2/243* (2013.01); *A61F 2/2418* (2013.01); *A61F 2002/9505* (2013.01); *A61F 2/9517* (2020.05); *A61F 2220/0033* (2013.01); *A61F 2230/0021* (2013.01)

(58) Field of Classification Search
CPC ....... A61F 2/243; A61F 2/2436; A61F 2/2439
See application file for complete search history.

(56) References Cited

U.S. PATENT DOCUMENTS

| | | | |
|---|---|---|---|
| 519,297 | A | 5/1894 | Wanek et al. |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Alvin J Stewart
(74) *Attorney, Agent, or Firm* — Klarquist Sparkman, LLP

(57) ABSTRACT

An assembly can include a prosthetic valve and a delivery apparatus having a handle and a plurality of actuator assemblies extending from the handle. The prosthetic valve can have a plurality of posts one or more of which are configured as actuators having an axially spaced first member and second member, and a threaded rod extending through first and second members. Each actuator assembly can include a first actuation member engaging an outflow end of the prosthetic valve and having first and second support extensions, and a second actuation member extending through the first actuation member and comprising a distal end portion having an engagement portion releasably coupled to the threaded rod. The first and second support extensions can inhibit rotation of the frame relative to the one or more actuator assemblies during expansion of the prosthetic valve.

19 Claims, 16 Drawing Sheets

(56) References Cited

U.S. PATENT DOCUMENTS

| | | | |
|---|---|---|---|
| 5,176,698 A | 1/1993 | Burns et al. | |
| 5,192,297 A | 3/1993 | Hull | |
| 5,266,073 A | 11/1993 | Wall | |
| 5,325,845 A | 7/1994 | Adair | |
| 5,358,496 A | 10/1994 | Ortiz et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 7,988,724 B2 * | 8/2011 | Salahieh | A61B 17/0644 |
| | | | 623/2.12 |
| 8,029,556 B2 | 10/2011 | Rowe | |
| 8,052,732 B2 * | 11/2011 | Mitchell | A61F 2/95 |
| | | | 623/1.11 |
| 8,167,932 B2 | 5/2012 | Bourang et al. | |
| RE43,882 E | 12/2012 | Hopkins et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 8,647,378 B2 * | 2/2014 | Mews | A61B 17/885 |
| | | | 623/1.11 |
| 8,894,703 B2 * | 11/2014 | Salahieh | A61F 2/2418 |
| | | | 623/2.11 |
| 9,061,119 B2 | 6/2015 | Le et al. | |
| 9,119,716 B2 | 9/2015 | Lee et al. | |
| 9,566,178 B2 * | 2/2017 | Cartledge | A61F 2/966 |
| 9,795,477 B2 | 10/2017 | Tran et al. | |
| 9,814,611 B2 * | 11/2017 | Cartledge | A61F 2/93 |
| 10,201,416 B2 * | 2/2019 | Backus | A61F 2/2436 |
| 10,226,335 B2 * | 3/2019 | Cartledge | A61F 2/2418 |
| 10,265,169 B2 * | 4/2019 | Desrosiers | A61F 2/2427 |
| 10,292,842 B2 * | 5/2019 | White | A61F 2/243 |
| 10,603,165 B2 * | 3/2020 | Maimon | A61F 2/2418 |
| 10,709,552 B2 * | 7/2020 | Backus | A61F 2/2403 |
| 10,869,759 B2 * | 12/2020 | Barash | A61F 2/243 |
| 10,874,508 B2 * | 12/2020 | Cartledge | A61F 2/2418 |
| 10,939,996 B2 * | 3/2021 | Adamek-Bowers | |
| | | | A61F 2/2418 |
| 11,083,576 B2 * | 8/2021 | Cartledge | A61F 2/2418 |
| 11,241,310 B2 * | 2/2022 | Loughnane | A61F 2/2439 |
| 11,273,038 B2 | 3/2022 | Tang et al. | |
| 11,344,408 B2 * | 5/2022 | Maimon | A61F 2/2418 |
| 11,707,356 B2 * | 7/2023 | Cartledge | A61F 2/844 |
| | | | 623/2.11 |
| 12,083,012 B2 * | 9/2024 | Maimon | A61F 2/2418 |
| 12,268,598 B2 * | 4/2025 | Cohen-Tzemach | |
| | | | A61F 2/2439 |
| 12,357,457 B2 * | 7/2025 | Schwarcz | A61F 2/2418 |
| 12,364,596 B2 * | 7/2025 | Cartledge | A61B 5/6862 |
| 12,364,598 B2 * | 7/2025 | Maimon | A61F 2/2418 |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno Azizi | |
| 2006/0025857 A1 | 2/2006 | Bergheim et al. | |
| 2006/0282150 A1 | 12/2006 | Olson et al. | |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203503 A1 * | 8/2007 | Salahieh | A61F 2/2436 |
| | | | 623/2.11 |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0103520 A1 | 5/2008 | Selkee | |
| 2008/0125853 A1 | 5/2008 | Bailey et al. | |
| 2008/0294230 A1 | 11/2008 | Parker | |
| 2009/0024428 A1 | 1/2009 | Hudock | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |

(56) References Cited

U.S. PATENT DOCUMENTS

| 2009/0228093 | A1 | 9/2009 | Taylor et al. | |
| 2009/0276040 | A1 | 11/2009 | Rowe et al. | |
| 2009/0281619 | A1 | 11/2009 | Le et al. | |
| 2009/0299456 | A1 | 12/2009 | Melsheimer | |
| 2009/0319037 | A1 | 12/2009 | Rowe et al. | |
| 2010/0030318 | A1 | 2/2010 | Berra | |
| 2010/0036472 | A1 | 2/2010 | Papp | |
| 2010/0036473 | A1 | 2/2010 | Roth | |
| 2010/0049313 | A1 | 2/2010 | Alon et al. | |
| 2010/0076402 | A1 | 3/2010 | Mazzone et al. | |
| 2010/0076541 | A1 | 3/2010 | Kumoyama | |
| 2010/0082089 | A1 | 4/2010 | Quadri et al. | |
| 2010/0094394 | A1 | 4/2010 | Beach et al. | |
| 2010/0121425 | A1 | 5/2010 | Shimada | |
| 2010/0145431 | A1 | 6/2010 | Wu et al. | |
| 2010/0161036 | A1 | 6/2010 | Pintor et al. | |
| 2010/0174363 | A1 | 7/2010 | Castro | |
| 2010/0198347 | A1 | 8/2010 | Zakay et al. | |
| 2010/0274344 | A1 | 10/2010 | Dusbabek et al. | |
| 2011/0015729 | A1 | 1/2011 | Jimenez et al. | |
| 2011/0054596 | A1 | 3/2011 | Taylor | |
| 2011/0137331 | A1 | 6/2011 | Walsh et al. | |
| 2011/0160846 | A1 | 6/2011 | Bishop et al. | |
| 2012/0123529 | A1 | 5/2012 | Levi et al. | |
| 2012/0239142 | A1 | 9/2012 | Liu et al. | |
| 2013/0030519 | A1 | 1/2013 | Tran et al. | |
| 2013/0046373 | A1* | 2/2013 | Cartledge | A61F 2/966 623/1.11 |
| 2013/0166017 | A1* | 6/2013 | Cartledge | A61F 2/2439 623/1.2 |
| 2013/0310923 | A1* | 11/2013 | Kheradvar | A61B 8/0841 623/2.11 |
| 2013/0317598 | A1 | 11/2013 | Rowe et al. | |
| 2014/0296962 | A1 | 10/2014 | Cartledge et al. | |
| 2017/0065415 | A1 | 3/2017 | Rupp et al. | |
| 2018/0153689 | A1 | 6/2018 | Maimon et al. | |
| 2018/0228610 | A1* | 8/2018 | Lashinski | A61F 2/2466 |
| 2018/0344456 | A1 | 12/2018 | Barash et al. | |
| 2019/0380829 | A1* | 12/2019 | Loughnane | A61F 2/243 |
| 2021/0282921 | A1* | 9/2021 | Schwarcz | A61B 5/1126 |
| 2022/0257367 | A1* | 8/2022 | Neumann | A61F 2/844 |
| 2022/0287838 | A1* | 9/2022 | Cohen | A61F 2/243 |
| 2022/0331132 | A1* | 10/2022 | Cohen | A61F 2/243 |
| 2022/0370198 | A1* | 11/2022 | Nir | A61F 2/2415 |
| 2023/0255752 | A1* | 8/2023 | Leichner | A61F 2/2418 623/2.1 |
| 2023/0338140 | A1* | 10/2023 | Cartledge | A61F 2/95 |
| 2025/0000648 | A1* | 1/2025 | Miller | A61F 2/2418 |
| 2025/0000649 | A1* | 1/2025 | Sirote | A61F 2/2418 |
| 2025/0009505 | A1* | 1/2025 | Harel | A61F 2/243 |

FOREIGN PATENT DOCUMENTS

| EP | 0592410 | B1 | 10/1995 |
| EP | 0850607 | A1 | 7/1998 |
| FR | 2815844 | A1 | 5/2002 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A1 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |

* cited by examiner

100

104

114

112

110

106

116

108

108

102

DELIVERY APPARATUS FOR MECHANICALLY EXPANDABLE VALVE

CROSS-REFERENCE TO RELATED APPLICATION

This application is a continuation of International Application No. PCT/US2021/052745, filed Sep. 30, 2021, which claims the benefit of U.S. Provisional Patent Application No. 63/085,947, filed on Sep. 30, 2020, for DELIVERY APPARATUS FOR MECHANICALLY EXPANDABLE VALVE, both of which are incorporated by reference herein in their entirety.

FIELD

The present disclosure relates to implantable; mechanically expandable prosthetic devices, such as prosthetic heart valves, and to methods and delivery assemblies for, and including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size, for example, by inflating a balloon on which the prosthetic valve is mounted, actuating a mechanical actuator that applies an expansion force to the prosthetic heart valve, or by deploying the prosthetic heart valve from a sheath of the delivery apparatus so that the prosthetic heart valve can self-expand to its functional size.

Prosthetic heart valves that rely on a mechanical actuator for expansion can be referred to as "mechanically expandable" prosthetic heart valves. Mechanically expandable prosthetic heart valves can provide one or more advantages over self-expandable and balloon-expandable prosthetic heart valves. For example, mechanically expandable prosthetic heart valves can be expanded to various diameters. Mechanically expandable prosthetic heart valves can also be compressed after an initial expansion (e.g., for repositioning and/or retrieval). However, some known devices and methods can cause rotation or movement of the prosthetic valve during expansion.

Despite the recent advancements in percutaneous valve technology, there remains a need for improved transcatheter heart valves and delivery devices for such valves.

SUMMARY

In a representative example, an assembly can include a prosthetic heart valve and a delivery apparatus. The prosthetic heart valve can include a radially expandable and compressible frame having an inflow end portion and an outflow end portion, the frame can comprise a plurality of actuator mechanisms each comprising a first frame member having a first inner bore and a second frame member having a second inner bore, the first and second frame members being spaced apart axially from one another, and a rod having an external threaded surface and extending through the first and second inner bores. The delivery apparatus can comprise a handle and one or more actuator assemblies extending from the handle. Each actuator assembly can include a first actuation member having a distal end portion releasably coupled to the outflow end portion of the frame, the distal end portion comprising first and second support extensions, and a second actuation member extending through the first actuation member and comprising a distal end portion having an engagement portion releasably coupled to the rod. Rotation of the second actuation member in a first direction can cause corresponding rotation of the rod such that the first and second frame members move axially toward one another to expand the prosthetic valve, and the first and second support extensions can inhibit rotation of the frame relative to the one or more actuator assemblies during expansion of the prosthetic valve.

In another representative example, an assembly can comprise a prosthetic heart valve and a delivery apparatus. The prosthetic heart valve can include a radially expandable and compressible frame having an inflow end portion and an outflow end portion, the frame comprising a plurality of actuation mechanisms each comprising a first frame member having a first inner bore and a second frame member having a second inner bore, the first and second frame members being spaced apart axially from one another, and a rod having an external threaded surface and extending through the first and second inner bores, a proximal end portion of the rod comprising first and second protrusions defining a slot between them, and first and second shoulders. The delivery apparatus can include a handle and one or more actuator assemblies extending from the handle, each actuator assembly comprising a first actuation member having a distal end portion abutting the outflow end portion of the frame, and a second actuation member extending through the first actuation member, the second actuation member comprising a distal end portion having a central protrusion extending into the slot and first and second flexible elongated elements releasably coupled to the shoulders. Rotation of the second actuation member in a first direction can cause corresponding rotation of the rod such that the first and second members move axially toward one another to expand the prosthetic valve.

In a representative example, a delivery apparatus can comprise a handle and one or more actuation assemblies extending from the handle. Each actuator assembly can comprise a first actuation member having a distal end portion configured to abut an outflow end portion of a prosthetic heart valve, the distal end portion comprising first and second support extensions, and a second actuation member extending through the first actuation member and having a distal end portion configured to releasably couple an actuator of the prosthetic heart valve. Rotation of the second actuation member in a first direction radially expands the prosthetic valve and rotation of the second actuation member in a second direction radially compresses the prosthetic valve. The first support extension is configured to extend partially over a portion of a radially inner surface of the prosthetic valve and the second support extension is configured to extend partially over a radially outer surface of the prosthetic valve to inhibit rotation of the frame of the prosthetic valve relative to the actuator assemblies.

In a representative example, an implantable prosthetic device can include a radially expandable and compressible frame having an inflow end portion and an outflow end portion, and a plurality of actuation mechanisms. Each actuation mechanism can comprise a first frame member having a first inner bore, and a second frame member having a second inner bore, the first and second frame members being spaced apart axially from one another. The frame can further include a plurality of struts coupling adjacent posts to one another, and a rod having an external threaded surface and extending through the first and second inner bores, a proximal end portion of the rod comprising first and second protrusions defining a slot between them, and first and second shoulders extending radially from an outer surface of the rod. Rotation of the rod in a first direction results in axial movement of the first and second frame members toward one another to radially expand the prosthetic device.

A representative method can include inserting a distal end of a delivery apparatus into the vasculature of a patient. The delivery apparatus can be releasably coupled to a prosthetic valve via a plurality of actuator assemblies. The prosthetic heart valve can include a frame comprising a plurality of actuation mechanisms each comprising a first frame member and a second frame member axially spaced from one another and a threaded rod extending through the first and second frame members. Each actuator assembly can include a first actuation member engaging an outflow end of the prosthetic valve and a second actuation member extending through the first actuation member and engaging an outflow end of the threaded rod, the first actuation member comprising a first support extension extending partially over a radially inner surface of the frame and a second support extension extending partially over a radially over surface of the frame. The method can further include advancing the prosthetic valve to a selected implantation site, and rotating the second actuation member to cause corresponding rotation of the threaded rod resulting in axial movement of the first and second frame members toward one another to radially expand the prosthetic valve, the first and second support extensions inhibiting rotation of the frame relative to the first actuation member during expansion.

In a representative example, an assembly can comprise a prosthetic heart valve and a delivery apparatus. The prosthetic heart valve can comprise a radially expandable and compressible frame having an inflow end portion and an outflow end portion, the frame comprising a plurality of actuation mechanisms, each comprising a first frame member having a first inner bore and a second frame member having a second inner bore, the first and second frame members being spaced apart axially from one another, and a rod having an external threaded surface and extending through the first and second inner bores. The delivery apparatus can comprise a handle and one or more actuator assemblies extending from the handle, each actuator assembly comprising a first actuation member having a distal end portion releasably coupled to the outflow end portion of the frame, the distal end portion can comprise first and second support extensions, and a second actuation member extending through the first actuation member and comprising a distal end portion having an engagement portion. The engagement portion can comprise a driver head having an engagement member that extends into a corresponding recess in the rod, and a gripper member comprising one or more arms releasably coupled to one or more projections extending from the rod. Wherein rotation of the second actuation member in a first direction causes corresponding rotation of the rod such that the first and second frame members move axially toward one another to expand the prosthetic valve, and wherein the first and second support extensions inhibit rotation of the frame relative to the one or more actuator assemblies during expansion of the prosthetic valve.

In a representative example, a delivery apparatus, can comprise a handle, and one or more actuator assemblies extending from the handle. Each actuator assembly can comprise a first actuation member having a distal end portion configured to abut an outflow end portion of a prosthetic heart valve, the distal end portion comprising first and second support extensions, and a second actuation member extending through the first actuation member and comprising a driver head having an engagement member configured to couple a corresponding engagement portion of the prosthetic heart valve, and a gripper member comprising one or more arms configured to releasably couple an actuator of the prosthetic heart valve. Wherein rotation of the second actuation member in a first direction is configured to radially expand the prosthetic valve and rotation of the second actuation member in a second direction is configured to radially compresses the prosthetic valve.

The foregoing and other objects, features, and advantages of the invention will become more apparent from the following detailed description, which proceeds with reference to the accompanying figures.

DETAILED DESCRIPTION

General Considerations

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

Figure 2:
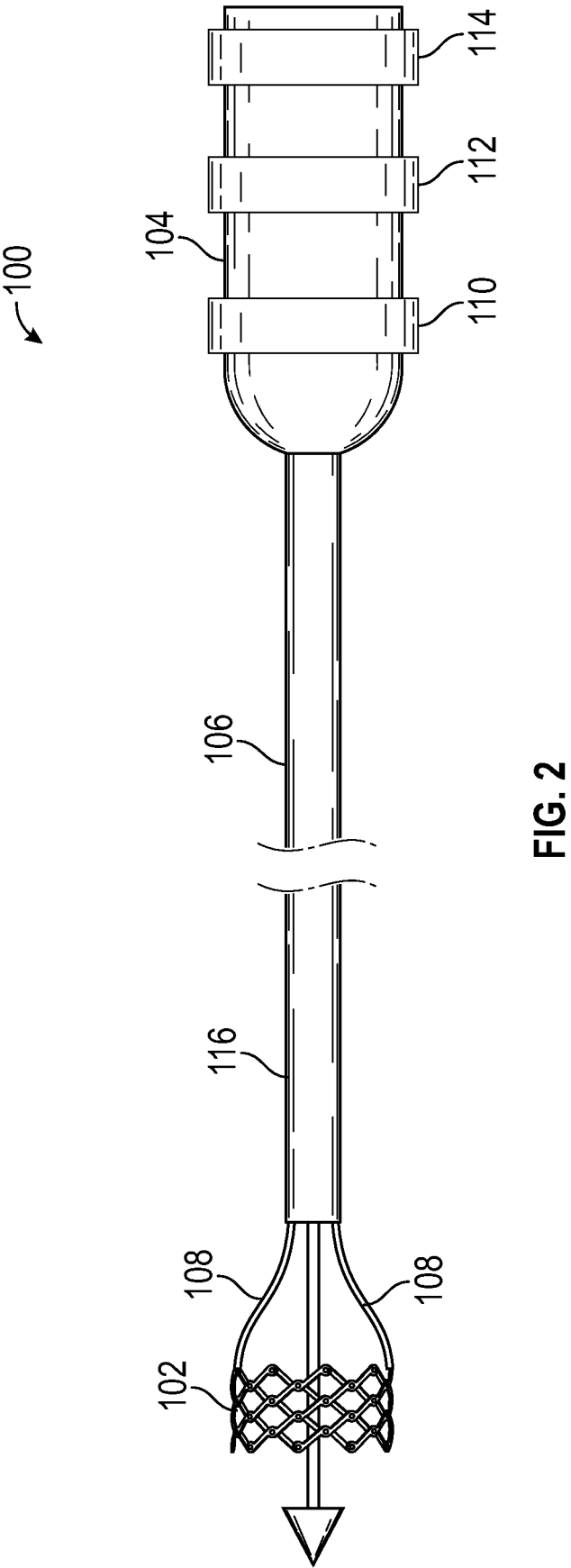
FIG. 2 is a side elevation view of a delivery apparatus for a prosthetic heart valve, according to one example.
Figure 3:
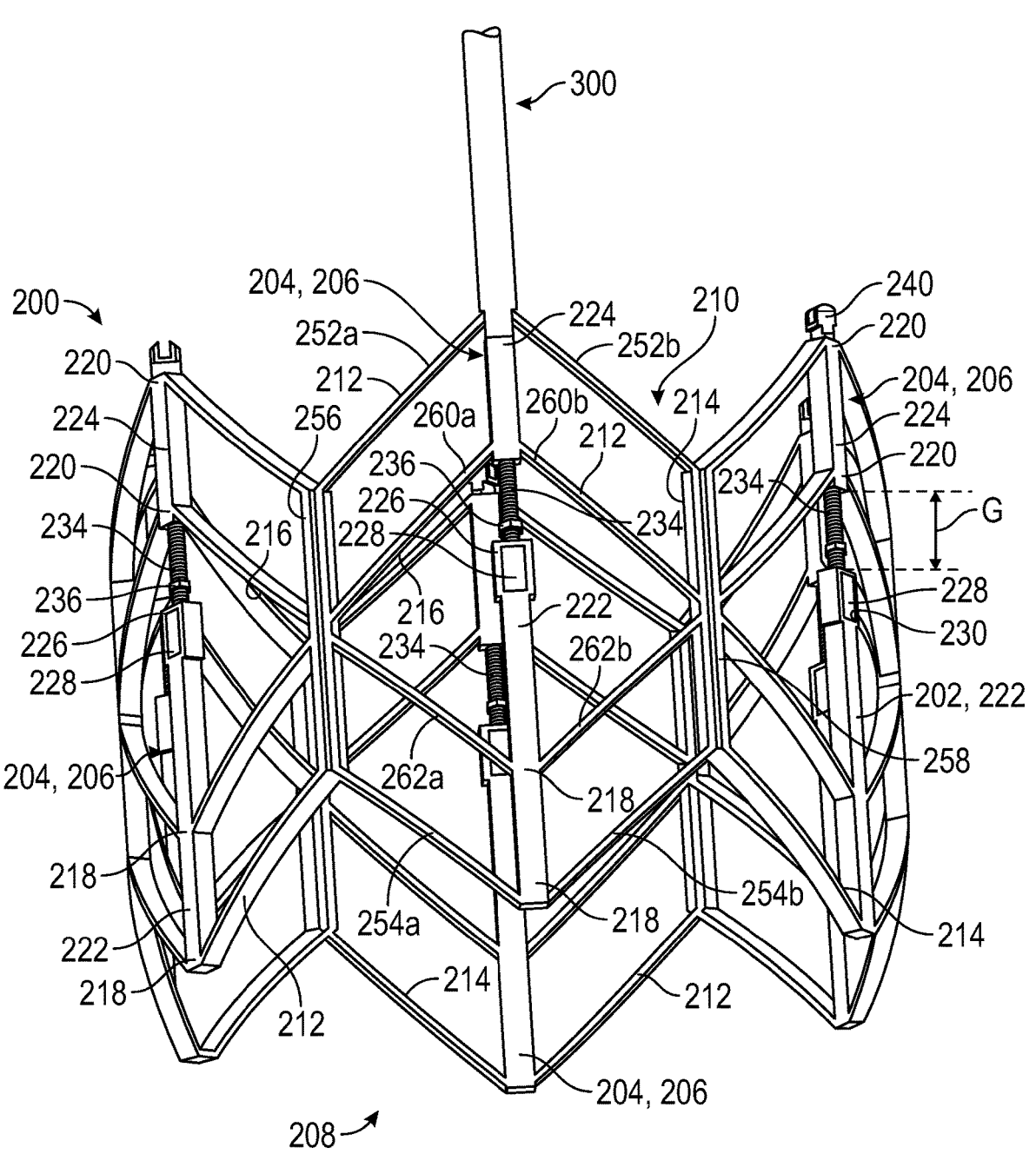
FIG. 3 is a perspective view of a frame of a prosthetic heart valve comprising a plurality of actuator mechanisms one of which is shown coupled to an actuator assembly of a delivery apparatus, according to one example.

All features described herein are independent of one another and, except where structurally impossible, can be used in combination with any other feature described herein. For example, a delivery apparatus 100 as shown in FIG. 2 can be used in combination with prosthetic valves 200 or 400 described herein. In another example, actuator mechanisms 206 as shown in FIG. 3 can be used in combination with the prosthetic valve 400 shown in FIG. 12 and/or prosthetic valve 10 shown in FIG. 1.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Examples of the Disclosed Technology

Described herein are examples of prosthetic implants, such as prosthetic heart valves, that can be implanted within any of the native valves of the heart (e.g., the aortic, mitral, tricuspid, and pulmonary valves). The present disclosure also provides frames for use with such prosthetic implants. The frames can further comprise actuator mechanisms (e.g., expansion mechanisms) and/or locking mechanisms to enable greater control over the radial compression or expansion of the valve body. The frames can comprise struts having different shapes and/or sizes to minimize the overall crimp profile of the implant and provide sufficient structural strength and rigidity to areas where needed.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the valves disclosed herein may be used with a variety of implant delivery apparatuses, and examples thereof will be discussed in more detail later.

Figure 1:
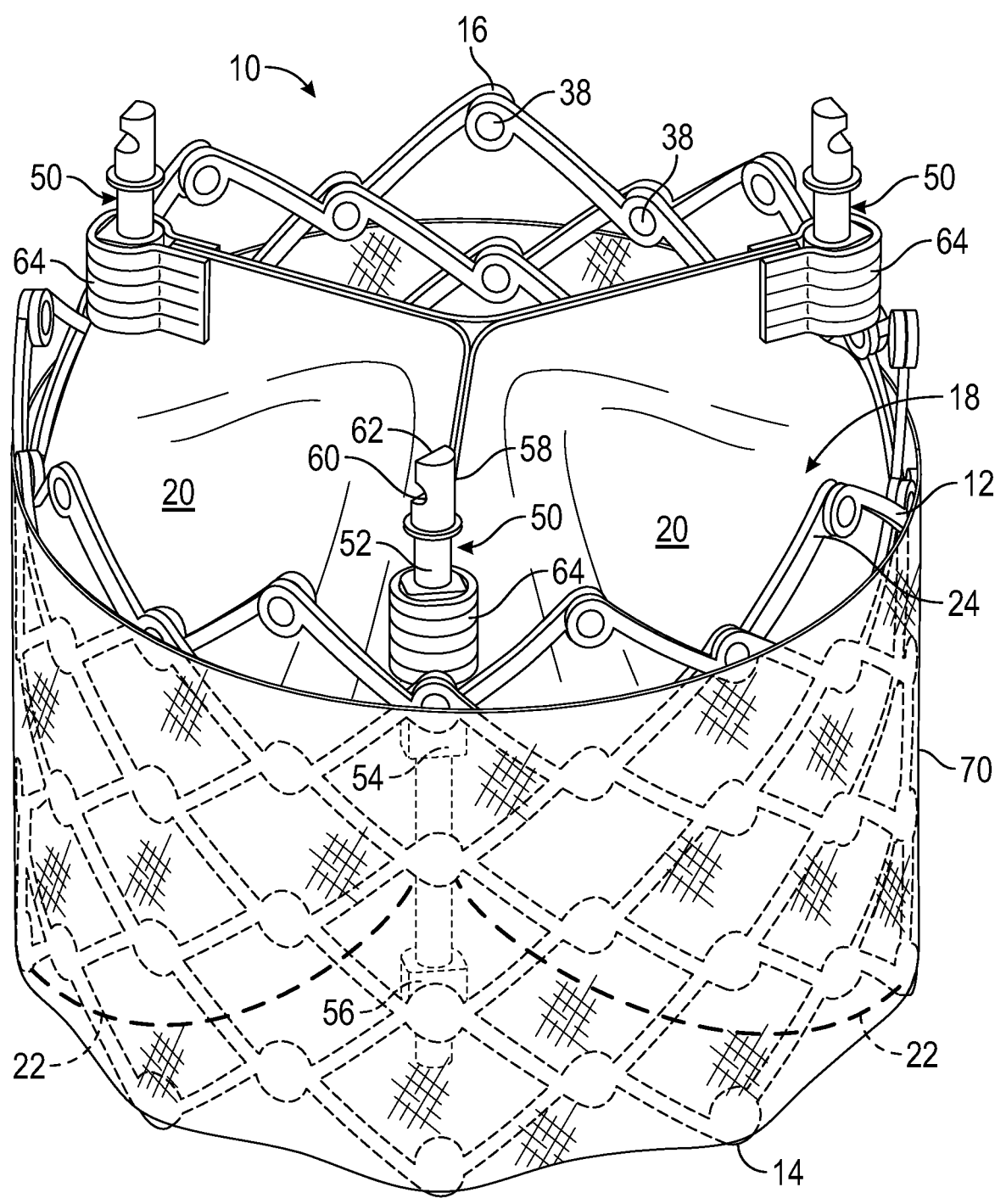
FIG. 1 is a perspective view of a prosthetic heart valve, according to one example.

FIG. 1 shows an exemplary prosthetic valve 10, according to one example. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures, each of which can be secured to a respective actuator mechanism 50 or the frame 12.

In the depicted example, the valvular structure 18 comprises three leaflets 20, which can be arranged to collapse in a tricuspid arrangement. Each leaflet 20 can have an inflow edge portion 22. As shown in FIG. 1, the inflow edge portions 22 of the leaflets 20 can define an undulating, curved scallop shape that follows or tracks a plurality of interconnected strut segments of the frame 12 in a circumferential direction when the frame 12 is in the radially expanded configuration. The inflow edges of the leaflets can be referred to as a "scallop line."

In some examples, the inflow edge portions 22 of the leaflets 20 can be sutured to adjacent struts of the frame generally along the scallop line. In other examples, the inflow edge portions 22 of the leaflets 20 can be sutured to an inner skirt, which in turn in sutured to adjacent struts of the frame. By forming the leaflets 20 with this scallop geometry, stresses on the leaflets 20 are reduced, which in turn improves durability of the valve 10. Moreover, by virtue of the scallop shape, folds and ripples at the belly of each leaflet 20 (the central region of each leaflet), which can cause early calcification in those areas, can be eliminated or at least minimized. The scallop geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, U.S. Publication No. 2018/0325665, and International Application No. PCT/US2020/024559, all of which are incorporated herein by reference in their entireties.

The prosthetic valve 10 can be radially compressible and expandable between a radially compressed configuration and a radially expanded configuration. The frame 12 can include a plurality of interconnected lattice struts 24 arranged in a lattice-type pattern and forming a plurality of apices 34 at the outflow end 16 of the prosthetic valve 10. The struts 24 can also form similar apices 32 at the inflow end 14 of the prosthetic valve 10.

The struts 24 can be pivotably coupled to one another at one or more pivot joints or pivot junctions 28 along the length of each strut. For example, in one example, each of the struts 24 can be formed with apertures 30 at opposing ends of the strut and apertures spaced along the length of the strut. Respective hinges can be formed at the locations where struts 24 overlap each other via fasteners 38, such as rivets or pins that extend through the apertures 30. The hinges can allow the struts 24 to pivot relative to one another as the frame 12 is radially expanded or compressed, such as during assembly, preparation, or implantation of the prosthetic valve 10.

The frame struts and the components used to form the pivot joints of the frame 12 (or any frames described below) can be made of any of various suitable materials, such as stainless steel, a cobalt chromium alloy, or a nickel titanium alloy ("NiTi"), for example Nitinol. In some examples, the frame 12 can be constructed by forming individual components (e.g., the struts and fasteners of the frame) and then mechanically assembling and connecting the individual components together. Further details regarding the construction of the frame and the prosthetic valve are described in U.S. Pat. Nos. 10,806,573, 10,603,165, and 10,869,759 and U.S. Patent Publication No. 2020/0188099, all of which are incorporated herein by reference.

In the illustrated example, the prosthetic valve 10 can be mechanically expanded from the radially contracted configuration to the radially expanded configuration. For example, the prosthetic valve 10 can be radially expanded by maintaining the inflow end 14 of the frame 12 at a fixed position while applying a force in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

As shown in FIG. 1, the prosthetic valve 10 can include one or more actuators 50 mounted to and equally spaced around the inner surface of the frame 12. Each of the actuators 50 can be configured to form a releasable connection with one or more respective actuators of a delivery apparatus.

In the illustrated example, expansion and compression forces can be applied to the frame by the actuators 50. Each of the actuators 50 can comprise a screw/actuation bolt/threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener 38 that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to foreshorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other examples, the actuators 50 can be reciprocating type actuators configured to apply axial directed forces to the frame to produce radial expansion and compression of the frame. For example, the rod 52 of each actuator can be fixed axially relative to the nut 56 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a subcomponent of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated examples, the prosthetic valve 10 includes three such actuators 50, although a greater or fewer number of actuators could be used in other examples. The leaflets 20 can have commissure attachments members 64 that wrap around the sleeves 54 of the actuators 50. Further details of the actuators, locking mechanisms and delivery apparatuses for actuating the actuators can be found in U.S. Pat. Nos. 10,603,165 and 10,806,573, U.S. Patent Publication No. 2018/0325665, and International Application Nos. PCT/US2020/057691 and PCT/US2021/022467, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The prosthetic valve 10 can include one or more skirts or sealing members. In some examples, the prosthetic valve 10 can include an inner skirt (not shown) mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. As shown in FIG. 1, the prosthetic valve 10 can also include an outer skirt 70 mounted on the outer surface of the frame 12. The outer skirt 70 can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials, including fabrics (e.g., polyethylene terephthalate fabric) or natural tissue (e.g., pericardial tissue). Further details regarding the use of skirts or sealing members in prosthetic valve can be found, for example, in U.S. Patent Publication No. 2020/0352711, which is incorporated herein by reference in its entirety.

FIG. 2 illustrates a delivery apparatus 100, according to one example, adapted to deliver a prosthetic heart valve 102, such as the illustrated prosthetic heart valve 10, described above. The prosthetic valve 102 can be releasably coupled to the delivery apparatus 100. It should be understood that the delivery apparatus 100 and other delivery apparatuses disclosed herein can be used to implant prosthetic devices other than prosthetic valves, such as stents or grafts.

The delivery apparatus 100 in the illustrated example generally includes a handle 104, a first elongated shaft 106 (which comprises an outer shaft in the illustrated example) extending distally from the handle 104, at least one actuator assembly 108 extending distally through the outer shaft 106. The at least one actuator assembly 108 can be configured to radially expand and/or radially collapse the prosthetic valve 102 when actuated.

Though the illustrated example shows two actuator assemblies 108 for purposes of illustration, it should be understood that one actuator 108 can be provided for each actuator on the prosthetic valve. For example, three actuator assemblies 108 can be provided for a prosthetic valve having three actuators. In other examples, a greater or fewer number of actuator assemblies can be present.

In some examples, a distal end portion 116 of the shaft 106 can be sized to house the prosthetic valve in its radially compressed, delivery state during delivery of the prosthetic valve through the patient's vasculature. In this manner, the distal end portion 116 functions as a delivery sheath or capsule for the prosthetic valve during delivery, The actuator assemblies 108 can be releasably coupled to the prosthetic valve 102. For example, in the illustrated example, each actuator assembly 108 can be coupled to a respective actuator of the prosthetic valve 102. Each actuator assembly 108 can comprise a support tube, an actuator member, and a locking tool. When actuated, the actuator assembly can transmit pushing and/or pulling forces to portions of the prosthetic valve to radially expand and collapse the prosthetic valve as previously described. The actuator assemblies 108 can be at least partially disposed radially within, and extend axially through, one or more lumens of the outer shaft 106. For example, the actuator assemblies 108 can extend through a central lumen of the shaft 106 or through separate respective lumens formed in the shaft 106.

The handle 104 of the delivery apparatus 100 can include one or more control mechanisms (e.g., knobs or other actuating mechanisms) for controlling different components of the delivery apparatus 100 in order to expand and/or deploy the prosthetic valve 102. For example, in the illustrated example the handle 104 comprises first, second, and third knobs 110, 112, and 114.

The first knob 110 can be a rotatable knob configured to produce axial movement of the outer shaft 106 relative to the prosthetic valve 102 in the distal and/or proximal directions in order to deploy the prosthetic valve from the delivery sheath 116 once the prosthetic valve has been advanced to a location at or adjacent the desired implantation location with the patient's body. For example, rotation of the first knob 110 in a first direction (e.g., clockwise) can retract the sheath 116 proximally relative to the prosthetic valve 102 and rotation of the first knob 110 in a second direction (e.g., counter-clockwise) can advance the sheath 116 distally. In other examples, the first knob 110 can be actuated by sliding or moving the knob 110 axially, such as pulling and/or pushing the knob. In other examples, actuation of the first knob 110 (rotation or sliding movement of the knob 110) can produce axial movement of the actuator assemblies 108 (and therefore the prosthetic valve 102) relative to the delivery sheath 116 to advance the prosthetic valve distally from the sheath 116.

The second knob 112 can be a rotatable knob configured to produce radial expansion and/or contraction of the prosthetic valve 102. For example, rotation of the second knob 112 can move the actuator member and the support tube axially relative to one another. Rotation of the second knob 112 in a first direction (e.g., clockwise) can radially expand the prosthetic valve 102 and rotation of the second knob 112 in a second direction (e.g., counter-clockwise) can radially collapse the prosthetic valve 102. In other examples, the second knob 112 can be actuated by sliding or moving the knob 112 axially, such as pulling and/or pushing the knob.

The third knob 114 can be a rotatable knob configured to retain the prosthetic heart valve 102 in its expanded configuration. For example, the third knob 114 can be operatively connected to a proximal end portion of the locking tool of each actuator assembly 108. Rotation of the third knob in a first direction (e.g., clockwise) can rotate each locking tool to advance the locking nuts to their distal positions to resist radial compression of the frame of the prosthetic valve, as described above. Rotation of the knob 114 in the opposite direction (e.g., counterclockwise) can rotate each locking tool in the opposite direction to decouple each locking tool from the prosthetic valve 102. In other examples, the third knob 114 can be actuated by sliding or moving the third knob 114 axially, such as pulling and/or pushing the knob.

Although not shown, the handle 104 can include a fourth rotatable knob operative connected to a proximal end portion of each actuator member. The fourth knob can be configured to rotate each actuator member, upon rotation of the knob, to unscrew each actuator member from the proximal portion of a respective actuator. As described above, once the locking tools and the actuator members are uncoupled from the prosthetic valve 102, they can be removed from the patient.

FIG. 3 illustrates an exemplary example of a prosthetic heart valve 200 comprising a unitary lattice frame 202. The prosthetic valve 200 can include a valvular structure comprising a plurality of leaflet (such as valvular structure 18 comprising leaflets 20) and inner and/or outer skirts, as previously described, though these components are omitted for purposes of illustration. The frame 202 can include one or more axially-extending struts or posts 204, one or more of which can be configured as integral expansion and locking mechanisms or actuator mechanisms 206 comprising an actuator 234 (such as a threaded rod) and first and second actuator struts/actuator posts 222, 224.

FIG. 3 illustrates the frame 202 in a partially expanded configuration and shows the frame 202 coupled to an actuator assembly 300 of a delivery apparatus (e.g., delivery apparatus 100).

The frame 202 can comprise an inflow end portion 208 (which is the distal end of the frame in the delivery configuration for the illustrated example) and an outflow end portion 210 (which is the proximal end portion of the frame in the delivery configuration for the illustrated example).

Figure 13:
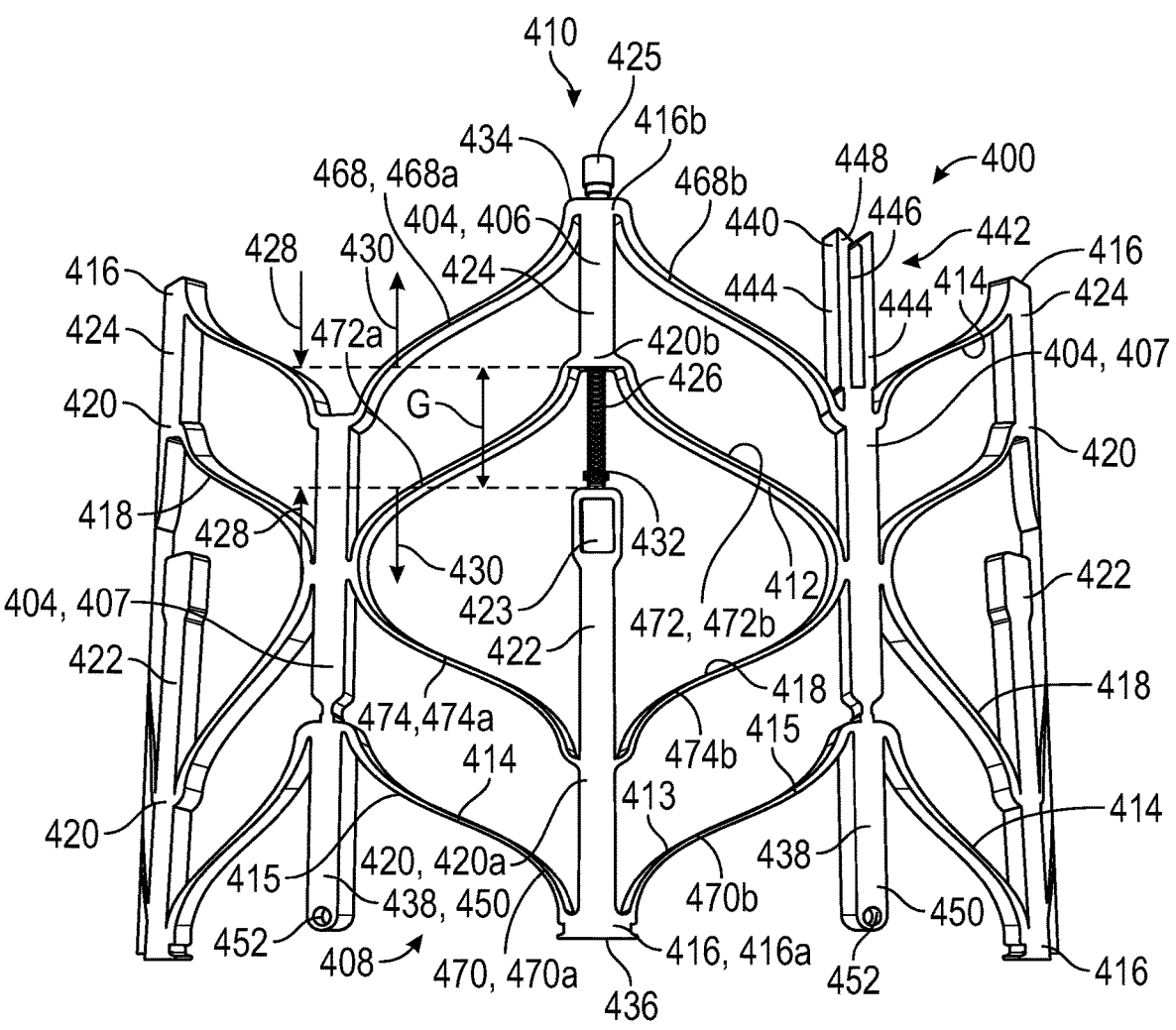
FIG. 13 is a perspective view of a portion of the frame of the prosthetic heart valve of FIG. 12.

As mentioned, the frame 202 can comprise a plurality of axially-extending struts or posts 204, one or more of which can be configured as actuator mechanisms 206. The actuator mechanisms 206 can include a plurality of first actuator struts or actuator posts 222 (which are lower posts in the illustrated example and can extend to the inflow end of the frame) and a plurality of second actuator struts or actuator posts 224 (which are upper posts in the illustrated example and can extend to the outflow end of the frame). Each first actuator post 222 can be axially aligned with a corresponding second actuator post 224 to form a pair of first and second posts. One or more pairs of actuator posts 222, 224 can be configured as part of an actuator mechanism 206. The actuator posts 204 can be coupled together by a plurality of link members or struts 212. For example, in the illustrated example, the struts 212 define a plurality of cells extending circumferentially around the frame 202. The circumferentially-extending cells can include relatively larger hexagonal cells 214, and relatively smaller diamond-shaped cells 216 disposed within the hexagonal cells 214. However, in other examples, the cells can have any of various other shapes, for example, triangular, tear drop shaped, rectangular, square, oval, square-oval, etc. For example, as described in more detail below, FIG. 13 illustrates another example of a prosthetic heart valve 400 including a frame 402 having a plurality of axially-extending struts or posts 404 coupled together by a plurality of curved link members or struts 412.

Each hexagonal cell 214 is formed by two upper struts 252a, 252b, two lower struts 254a, 254b, and two axial struts 256, 258, each extending between and connecting respective ends of an upper strut 252a, 252b and a lower strut 254a, 254b. The upper struts 252a, 252b can be part of an upper row of struts that defines the outflow end of the frame and the lower struts 254a, 254b can be part of a lower row of struts that defines the inflow end of the frame. Each diamond-shaped cell 216 is formed by two upper struts 260a, 260b and two lower struts 262a, 262b. The lower ends of the upper struts 260a, 260b and the upper ends of the lower struts 262a, 262b can be connected to the axial struts 256, 258. The upper ends of upper struts 252a, 252b of each hexagonal cell 214 can be connected to a second post 224 and the upper ends of upper struts 260a, 260b of the corresponding diamond-shaped cell 216 can be connected to the same second post 224. The lower ends of lower struts 254a, 254b of each hexagonal cell 214 can be connected to a first post 222 and the lower ends of lower struts 262a, 262b of the corresponding diamond-shaped cell 216 can be connected to the same first post 222.

In the illustrated example, there is one row of hexagonal cells 214 and one row of diamond-shaped cells 216. In alternative examples, the frame 202 can include a plurality of rows of hexagonal cells 214 and a plurality of rows of diamond-shaped cells 216 arrayed along the length of the frame, wherein the diamond-shaped cells 216 are positioned within the hexagonal cells.

The hexagonal and diamond cells 214, 216 can each comprise a respective inflow apex 218 and outflow apex 220. Each pair of actuator posts 222, 224 can extend through and be coupled to the inflow and outflow apices 218, 220 of a respective hexagonal cell 214 and diamond cell 216 pair. In the illustrated example, the frame 202 comprises six hexagonal cells 214 extending circumferentially in a row, with a diamond-shaped cell 216 within each hexagonal-shaped cell 214, and six pairs of actuator posts 222, 224 coupled to a respective pair of cells 214, 216. However, in other examples, the frame 202 can comprise a greater or fewer number of hexagonal cells 214 within a row, and a corresponding greater or fewer number of diamond cells 216, and/or pairs of actuator posts 222, 224.

In some examples, each pair of actuator posts 222, 224 can comprise part of an actuator mechanism 206 in combination with an actuator/threaded rod 234. For example, in the illustrated example, the frame comprises six pairs of posts 222, 224, each of which is configured as part of an actuator mechanism 206. In other examples, the frame 202 can comprise a greater or fewer number of actuator posts, and not all of the pairs of posts 222, 224 need to be actuator posts. Where a pair of posts 222, 224 is configured as part of an actuator mechanism, an actuator/screw/actuation bolt/threaded rod 234 extends through each actuator post 222, 224 of the pair to effect radially compression and expansion of the frame, as further described below. If a pair of posts 222, 224 is not configured as part of an actuator mechanism, an actuator/threaded rod 234 need not extend through the posts 222, 224 of that pair and the posts 222, 224 need not include the other features that are described below for radially compressing and expanding the frame.

Though in the illustrated example the actuator 234 is shown as a threaded rod, in other examples the actuator can be any of various members and/or mechanisms configured to move the first and second actuator posts 222, 224 axially relative to one another. For example, in other examples, the actuator 234 can be a linear rack comprising a plurality of teeth and configured to engage a corresponding pawl on the first and/or second actuator posts, or vice versa.

The upper end of each first actuator post 222 and the lower end of a corresponding second actuator post 224 can be separated by a gap G, allowing the actuator posts 222, 224 to move toward and away from each other during radial expansion and radial compression, respectively, of the frame. In the description that follows, the first and second actuator posts 222, 224, respectively, that are part of actuator mechanisms (i.e., those that include threaded rods 234), can also be referred to as first and second actuator frame members 222, 224, or more simply, first and second frame members 222, 224.

Each actuator frame member 222, 224 can comprise an inner bore 232 (FIG. 11) extending along a length of the frame member 222, 224 and through which a threaded rod 234 can extend. An outflow end portion 226 of the first frame member 222 can comprise or house a nut 228. In certain examples, the nut 228 can be separately formed from the frame member 222, which can be formed with a cut-out region defining window 230 in the outflow end portion of the frame member. The nut 228 can be positioned or housed within the cut-out region. As shown in FIG. 3, the nut 228 can be visible through the window 230. The nut 228 can comprise an inner threaded bore configured to engage the threads of the threaded rod 234 such that rotation of the threaded rod 234 causes the first frame member 222, which is coupled to the nut 228 to move relative to the second frame member 224, which is held steady.

In other examples, in lieu of using a nut 228, a portion of the inner bore 232 of the first frame member 222 can be threaded. For example, an outflow end portion of the first frame member 222 can comprise inner threads configured to engage the threaded rod 234 such that rotation of the threaded rod causes the first frame member 222 to move relative to the second frame member 224. In still other examples, the inner bore 232 of the first frame member 222 may be threaded along its entire length. In alternative examples, each second frame member 224 can have internal threads or can house a nut 228 that can engage external threads of a threaded rod 234.

Rotation of the threaded rod 234 in a first direction (e.g., clockwise) causes corresponding axial movement of the first and second frame members 222, 224 toward one another, expanding the frame 202, and rotation of the threaded rod 234 in a second direction (e.g., counterclockwise) causes corresponding axial movement of the first and second frame members 222, 224 away from one another, compressing the frame. As the frame 202 moves from a compressed configuration to an expanded configuration, the gap G between the first and second frame members 222, 224 of the actuator mechanism 206 can narrow. The threaded rod 234 can comprise a stopper 236 (such as in the form of a nut) disposed thereon. As shown in FIG. 3, the stopper 236 can be disposed on the threaded rod 234 such that it sits within the gap G. During crimping/compression of the prosthetic valve 200, the threaded rod 234 can be rotated in the second direction (e.g., counterclockwise) causing the stopper 236 to move toward the outflow end portion 210 of the frame 202 until it abuts the inflow edge of the second frame member 224, thereby preventing over-crimping of the frame 202.

Figure 4:
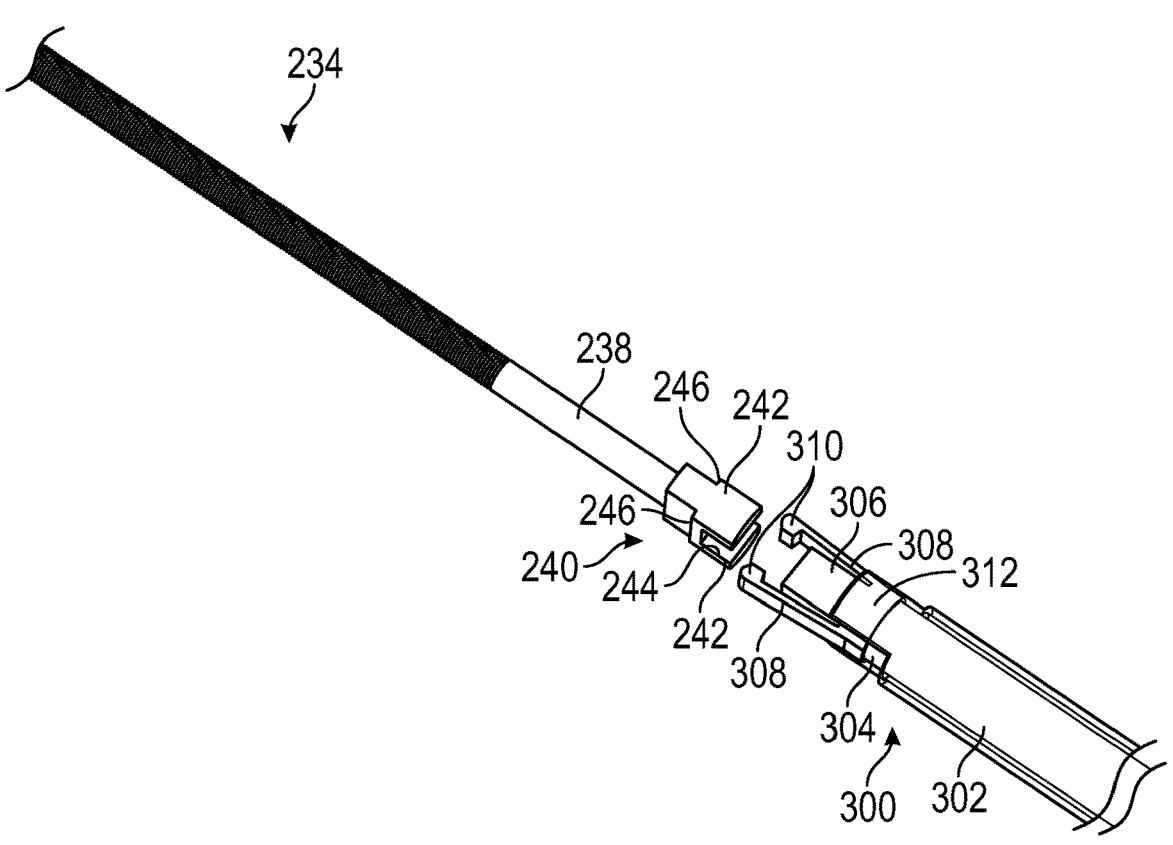
FIG. 4 is a perspective view of a portion of an actuator mechanism and actuator assembly of FIG. 3.
Figure 11:
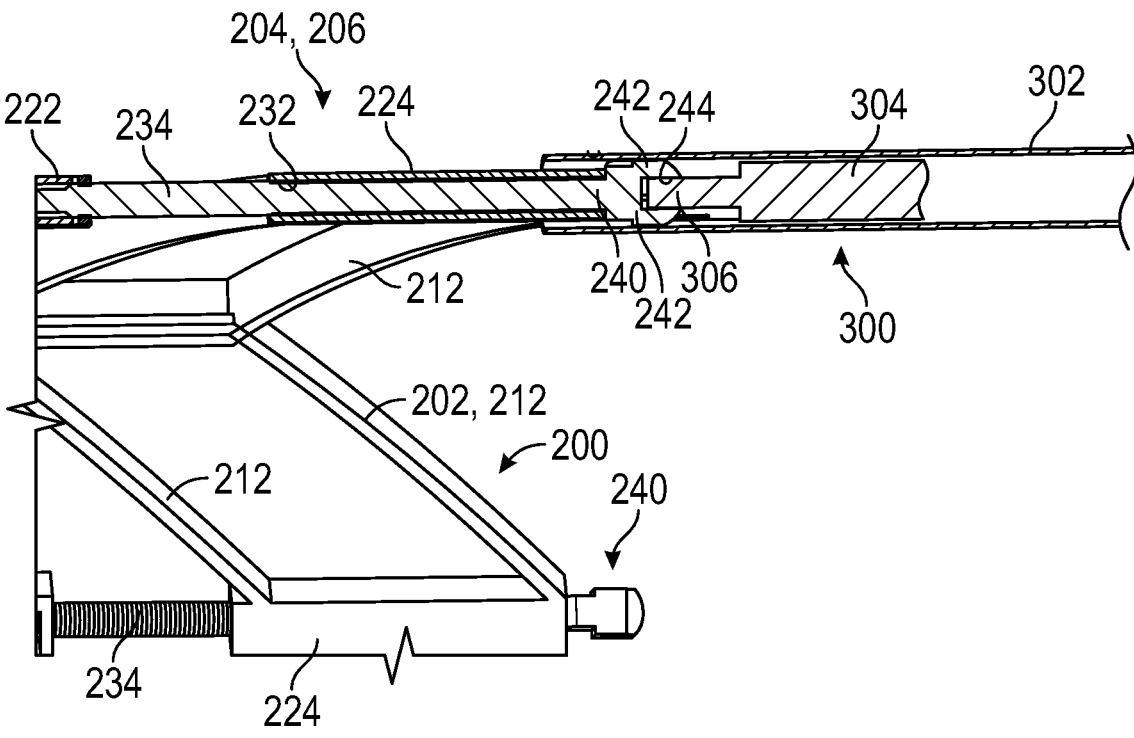
FIG. 11 is a partial cross-sectional view of a portion of the frame and actuator assembly of FIG. 3 shown coupled together.

Referring to FIG. 4, the outflow or proximal end portion 238 of each threaded rod 234 can comprise a head portion 240 configured to be releasably coupled to a respective actuator assembly 300. The head portion 240 can comprise first and second protrusions 242 defining a channel or slot 244 between them, and one or more shoulders 246. As shown in FIG. 11, the head portion 240 can have a width greater than a diameter of the inner bore 232 such that the head portion 240 is prevented from moving into the inner bore 232 of the second frame member 224 and such that the head portion 240 abuts the outflow end portion 210 of the frame 402. The head portion 240 can be used to apply a distally-directed force to the second frame member 224, for example, during radial expansion of the frame 402.

Rotation of the threaded rod 234 while holding the second frame member 224 steady at a fixed location relative to the distal apparatus and the surrounding anatomy (e.g., using an actuator assembly 300 of the delivery apparatus) or applying a distally-directed force to the second frame member 224 causes axial movement of the inflow end 208 and outflow end 210 relative to one another to cause radial expansion or compression of the frame 202. For example, moving the inflow and outflow ends 208, 210 toward one another causes the frame to foreshorten axially and expand radially. Conversely, moving the inflow and outflow ends 208, 210 away from one another causes the frame 202 to elongate axially and compress radially.

As shown in FIGS. 4-11, the threaded rod 234 of each actuator mechanism 206 can be releasably coupled to a respective actuator assembly 300 of a delivery apparatus, such as delivery apparatus 100, described previously. Referring to FIG. 4, each actuator assembly 300 can comprise a first actuation member configured as a support tube or outer sleeve 302 and a second actuation member configured as a driver 304. The driver 304 can extend through the outer sleeve 302. The outer sleeve 302 is shown transparently in FIGS. 4-6 and 9 for purposes of illustration. The distal end portions of the outer sleeve 302 and driver 304 can be configured to engage or abut the proximal end (e.g., the outflow end) of the threaded rod 234 and/or the frame 202. The proximal portions of the outer sleeve 302 and driver 304 can be operatively coupled to the handle of a delivery apparatus (e.g., handle 104). The delivery apparatus in this example can include the same features described previously for delivery apparatus 100. In particular examples, the proximal end portions of each driver 304 can be operatively connected to the knob 112 such that rotation of the knob 112 (clockwise or counterclockwise) causes corresponding rotation of the drivers 304. The proximal end portions of each outer sleeve 302 can be operatively connected to the knob 114 such that rotation of the knob 114 (clockwise or counterclockwise) causes corresponding axial movement of the sleeves 302 (proximally or distally) relative to the drivers 304. In other examples, the handle can include electric motors for actuating these components.

Figure 5:
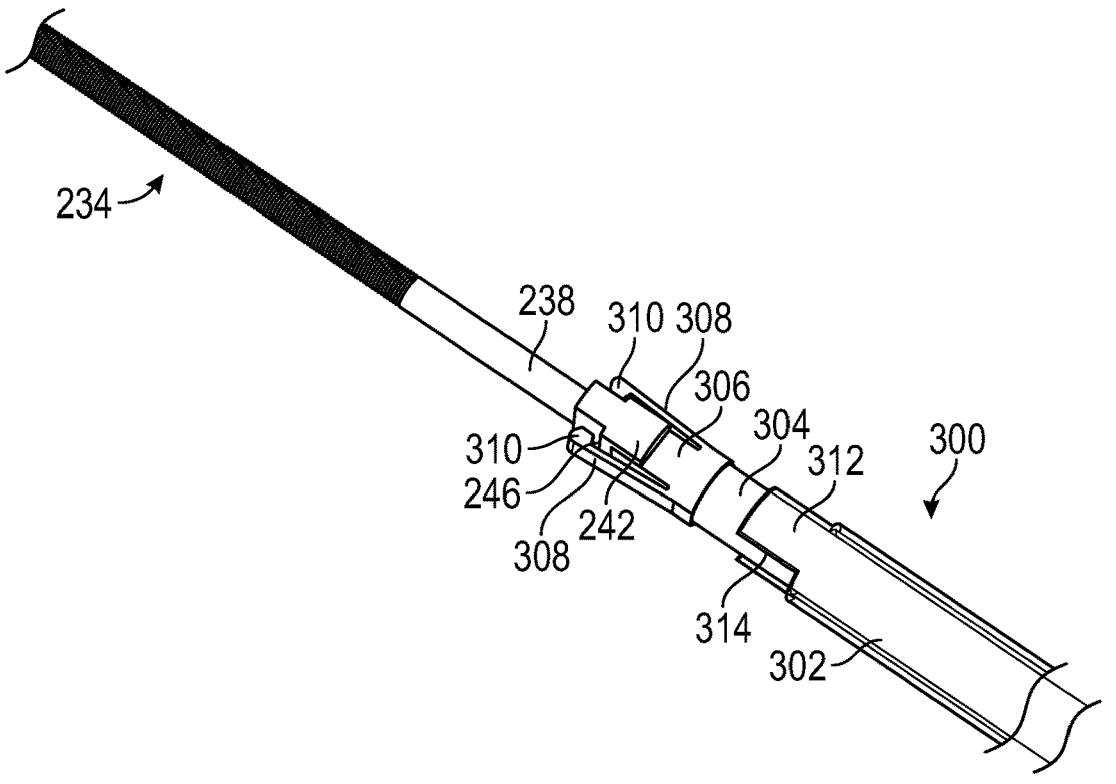
FIG. 5 is a perspective view of a portion of the actuator mechanism and actuator assembly of FIG. 4.

The distal end portion of the driver 304 can comprise a central protrusion 306 configured to extend into the slot 244 of the threaded rod 234, and one or more flexible elongated elements 308 including protrusions or teeth 310 configured to be releasably coupled to the shoulders 246 of the threaded rod 234. The protrusions 310 can extend radially inwardly toward a longitudinal axis of the driver/second actuation member 304. As shown in FIGS. 4-5, the elongated elements 308 can be configured to be biased radially outward to an expanded state, for example, by shape setting the elements 308.

Figure 6:
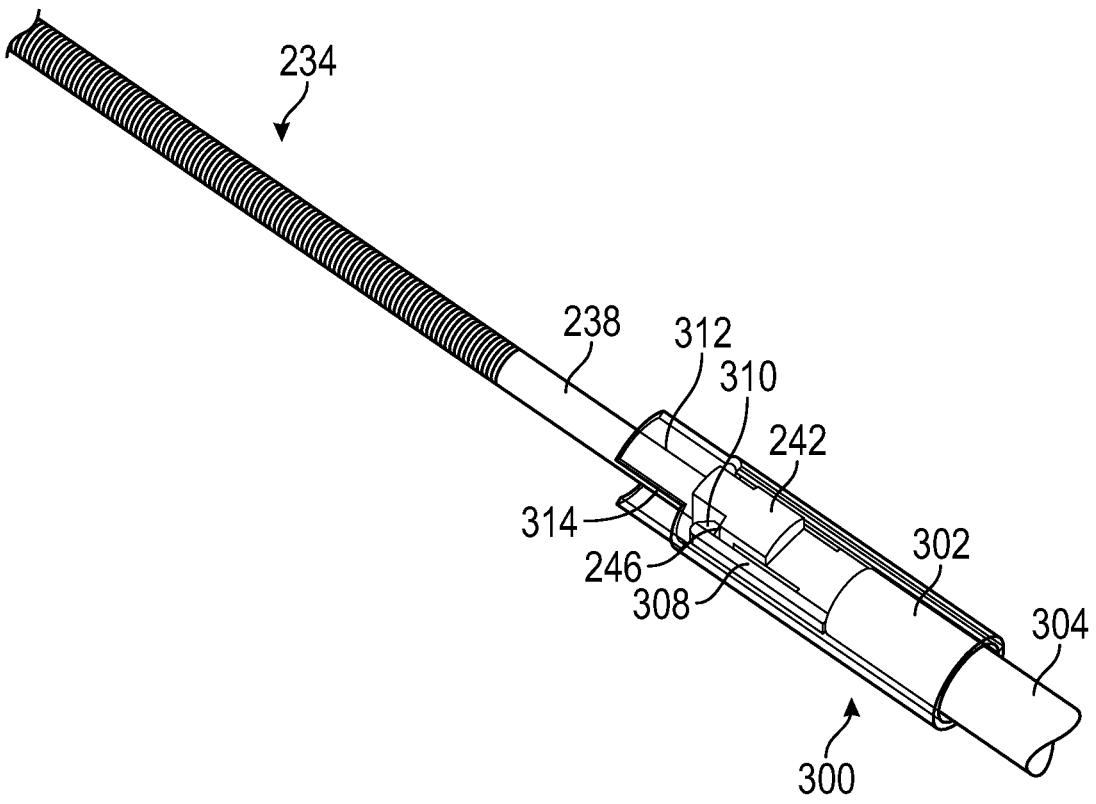
FIG. 6 is a perspective view of a portion of the actuator mechanism and actuator assembly of FIG. 4 with the outer sleeve shown transparently.
Figure 8:
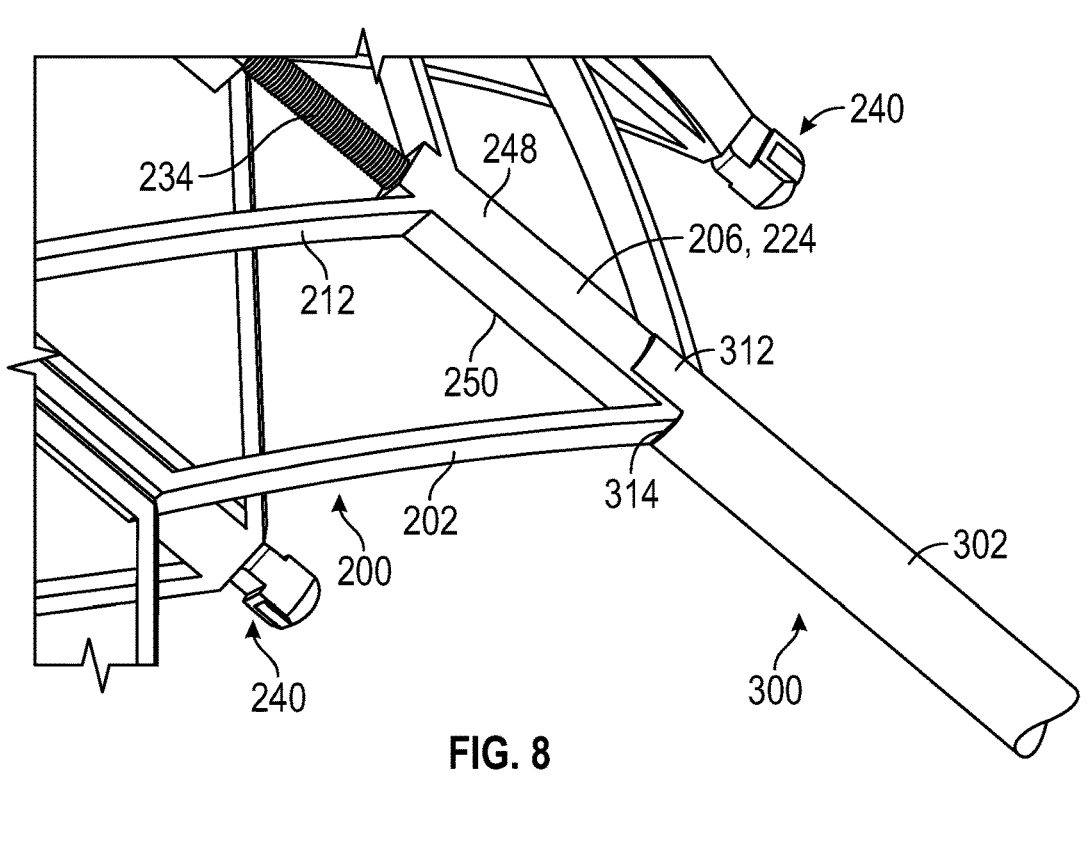
FIG. 8 is a perspective view of a portion of the frame and actuator assembly of FIG. 3 shown coupled together.
Figure 9:
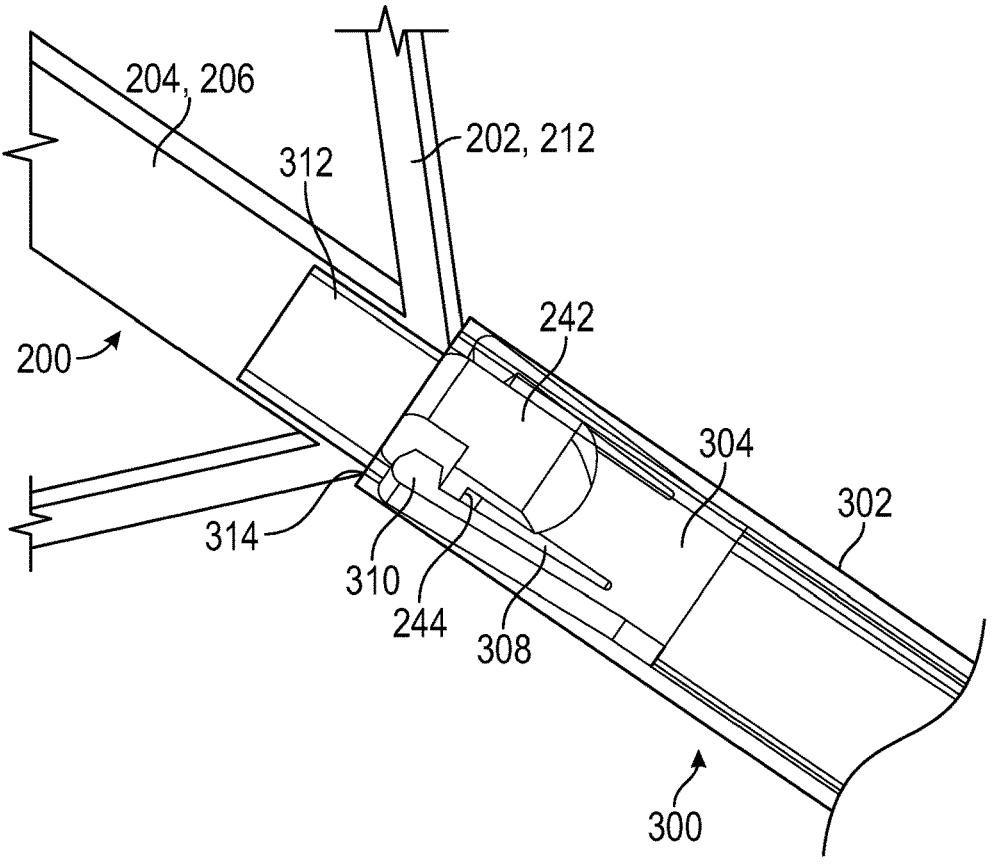
FIG. 9 is a perspective view of a portion of the frame and the actuator assembly of FIG. 3 shown coupled together with the outer sleeve shown transparently.
Figure 10:
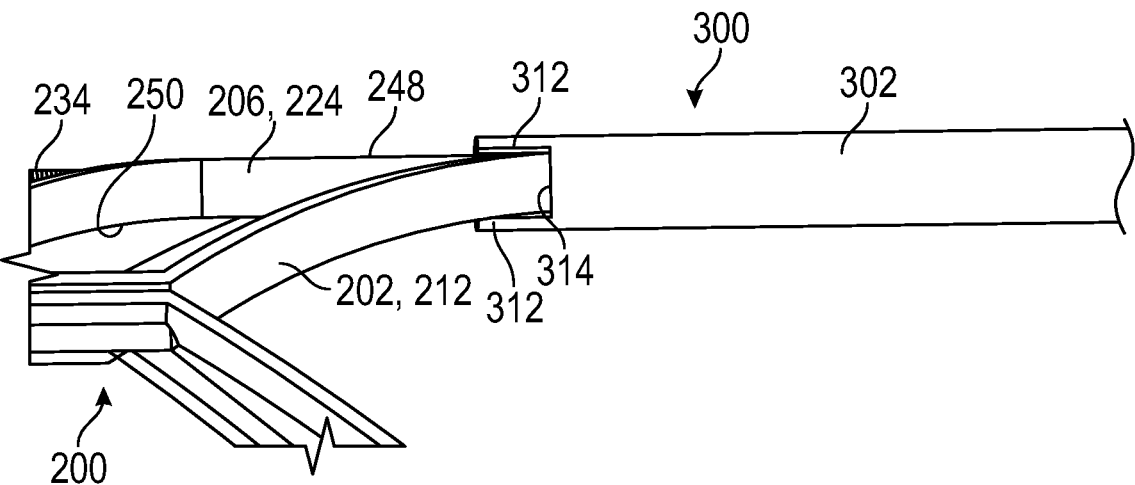
FIG. 10 is a perspective view of a portion of the frame and actuator assembly of FIG. 3 shown coupled together.

As shown in FIG. 5, to couple the actuator assembly 300 to the threaded rod 234, the driver 304 can be positioned such that the central protrusion 306 is disposed within the slot 244 (FIG. 4) and such that the protrusions 310 of the elongated elements 308 are positioned distally to the shoulders 246. Referring to FIG. 6, as the outer sleeve 302 is advanced (e.g., distally) over the driver 304, the elongated elements 308 are radially compressed until the protrusions 310 abut the shoulders 246, thereby coupling the actuator assembly 300 to the threaded rod 234. The outer sleeve 302 can continue to be advanced until the outer sleeve 302 engages the frame 202, as shown in FIG. 8. So coupled, the driver 304 can be rotated (e.g., using the handle of the delivery apparatus 100) to cause corresponding rotation of the threaded rod 234. The central protrusion 306 can be configured (e.g., sized and shaped) such that it is advantageously spaced apart from the inner walls of the outer sleeve 302, such that the central protrusion 306 does not frictionally contact the outer sleeve 302 during rotation.

Though in the illustrated example the central protrusion 306 has a substantially rectangular shape in cross-section, in other examples, the protrusion 306 can have any of various shapes, for example, square, triangular, oval, etc. The slot 244 can be correspondingly shaped to receive the protrusion 306.

Figure 7:
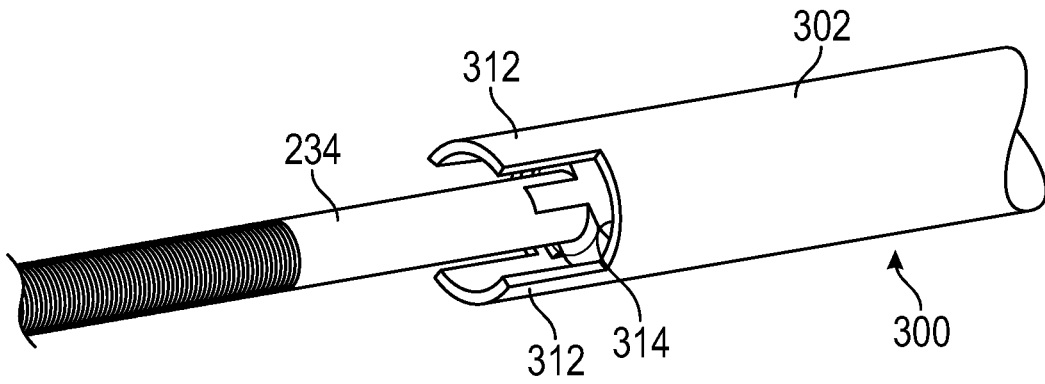
FIG. 7 is a perspective view of a portion of the actuator mechanism and actuator assembly of FIG. 4.

Referring now to FIG. 7, the distal end portion of the outer sleeve 302 can comprise first and second support extensions 312 defining gaps or notches 314 between the extensions 312. As shown in FIG. 8, the support extensions 312 can be oriented such that, when the actuator assembly 300 is coupled to a respective actuator mechanism 206, the support extensions 312 extend partially over a proximal end portion (e.g., the upper end portion) of the second frame member 224, and in particular, a radially outer surface 248 and a radially inner surface 250 of the second frame member 224. The engagement of the support extensions 312 with the frame 202 counter-acts rotational forces applied to the frame by the rods 234 during expansion of the frame. In the absence of a counter-force acting against these rotational forces, the frame tends to "jerk" or rock in the direction of rotation of the rods when they are actuated to expand the frame. The illustrated configuration is advantageous in that outer sleeves, when engaging the second frame members 224, can prevent or mitigate such jerking or rocking motion of the frame when the frame is expanded.

A prosthetic valve 200 including one or more actuator mechanisms 206 can be expanded in the following exemplary manner. Generally, the prosthetic valve 200 is placed in a radially compressed state and releasably coupled to one or more actuator assemblies 300 of a delivery apparatus (such as delivery apparatus 100 shown in FIG. 2), as described above, and the delivery apparatus and the prosthetic valve can be advanced over a guidewire through the vasculature of a patient to a selected implantation site (e.g., the native aortic annulus). For example, when implanting the prosthetic valve within the native aortic valve, the delivery apparatus and the prosthetic valve can be inserted into and through a femoral artery, and through the aorta to the native aortic valve. The prosthetic valve 200 can then be deployed at the implantation site (e.g., within the native aortic valve) and can be expanded and locked in the expanded configuration using the actuator mechanisms 206. Once a selected diameter of the prosthetic valve 200 is reached, the actuator assemblies 300 can be uncoupled from the actuator mechanisms 206 and removed from the patient's body.

To deploy the prosthetic valve 200, the physician can actuate the actuator assemblies 300 by rotating the drivers 304 in a first direction (e.g., by rotating the knob 112 or actuating a motor), which can cause corresponding rotation of the threaded rods 234. The rotation of the threaded rod 234 can cause axial movement of the first and second frame members 222, 224 of the actuator mechanism 206 toward one another to decrease the distance between the frame members 222, 224, causing the frame 202 to foreshorten axially and expand radially until a selected diameter is achieved. The disclosed actuator mechanism examples advantageously allow for continuous prosthetic valve expansion (e.g., without the stepped expansion that results from a ratcheting mechanism) and allow the prosthetic heart valve to be deployed at any of various diameters.

Once the prosthetic valve 200 has been implanted at a selected implantation site within a patient, the patient's native anatomy (e.g., the native aortic annulus) may exert radial forces against the prosthetic valve 200 that would tend to compress the frame 202. However, the engagement of the threaded rod 234 with the threaded nut 228 prevents such forces from compressing the frame 202, thereby ensuring that the frame remains locked in the desired radially expanded state.

If repositioning or recapture and removal of the prosthetic valve 200 is desired, the prosthetic valve can be compressed (from an expanded or partially expanded configuration) by rotating the drivers 304 and therefore the threaded rods 234 in a second, opposing direction. The rotation of the threaded rods 234 can cause axial movement of the first and second frame members 222, 224 of the actuator mechanism 206 away from one another to increase the distance between the frame members 222, 224, causing the frame 202 to elongate axially and compress radially. Once the prosthetic valve 200 has been recompressed it can be repositioned at the implantation site, once repositioned, the prosthetic valve 200 can be expanded as described previously. The prosthetic valve can be re-compressed, repositioned, and re-expanded multiple times, as needed. In some cases, the prosthetic valve 200 can be fully compressed and "recaptured," that is, retracted back into a sheath and/or removed from the patient's body.

Once final positioning and expansion of the prosthetic valve is achieved, the actuator assemblies 300 can be released from the prosthetic valve 200 by retracting the sleeves 302 to uncover the connection between the drivers 304 and the rods 234. This can be achieved by rotating the knob 114 or actuating a motor in the handle of the delivery apparatus. When each sleeve 302 is retracted, the expandable elements 308 of the driver 304 can expand outwardly and away from the shoulders 246 of the head portion 240 of the rod 234, thereby decoupling the driver 304 from the rod 234. At this stage, the delivery apparatus (including all of the actuator assemblies 300) can be retracted relative to the prosthetic valve 200 and removed from the patient's body.

Figure 12:
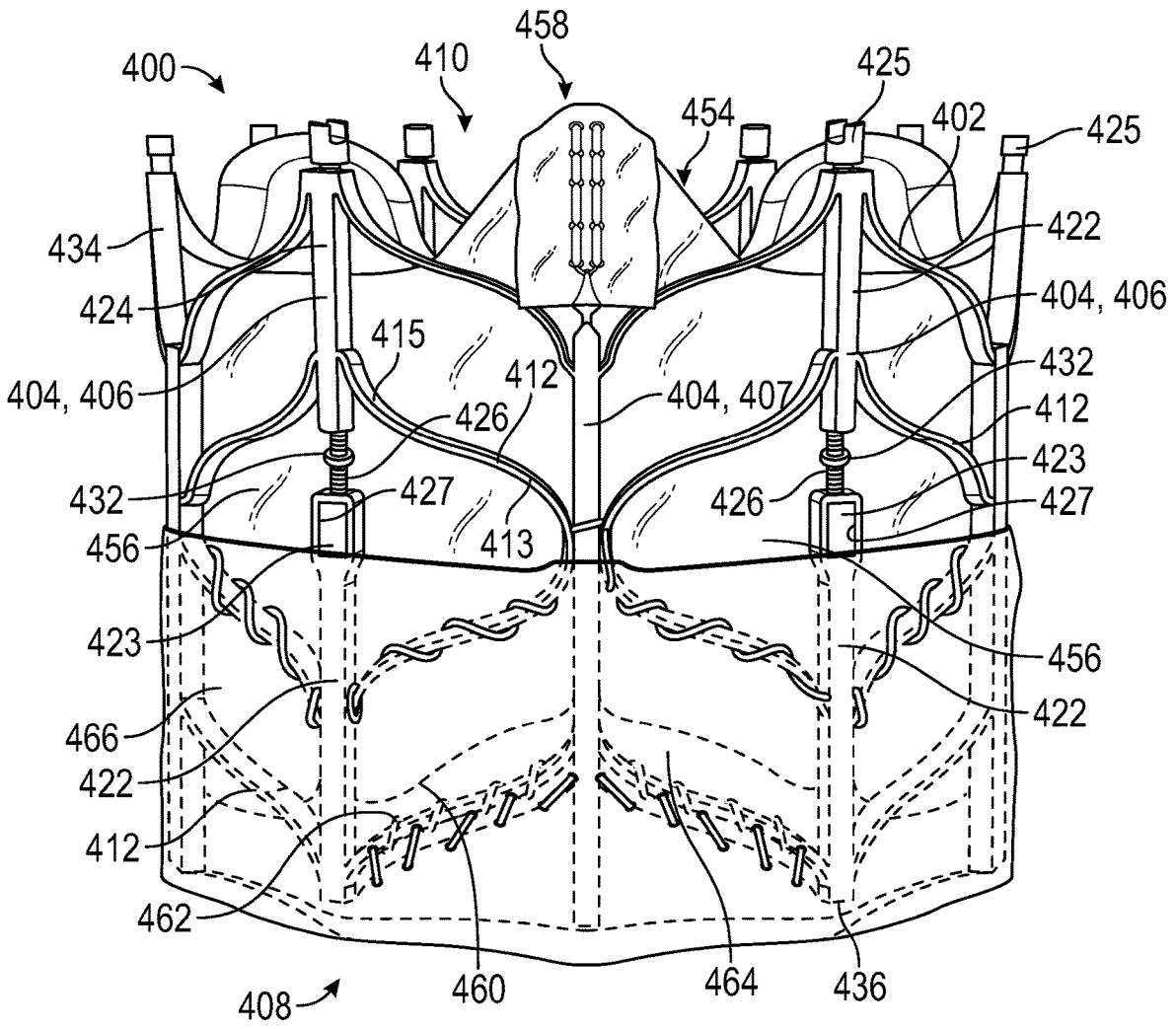
FIG. 12 is a perspective view of a prosthetic heart valve, according to one example.

FIG. 12 illustrates an example of a prosthetic valve 400 having a frame 402 including an inflow end portion 408 and an outflow end portion 410. The prosthetic valve 400 can further include a valvular structure 454, which is coupled to and supported inside the frame 402. The valvular structure 454 is configured to regulate the flow of blood through the prosthetic valve 400 from the inflow end 408 to the outflow end 410.

The prosthetic valve 400 can be similar to prosthetic valve 200, described above, including a frame 402 comprising a plurality of axially-extending posts 404, one or more of which (in combination with an actuator 426 such as a threaded rod) can be configured as actuator mechanisms 406, coupled together via a plurality of link members or struts 412. The prosthetic valve 400 in this example can include the same features described previously for prosthetic valve 200 and can be coupled to an actuator assembly 300 and expanded as described above for prosthetic valve 200.

The valvular structure 454 can include, for example, a leaflet assembly comprising one or more leaflets 456 made of flexible material. The leaflets 456 can be made from in whole or part, biological material, bio-compatible synthetic materials, or other such materials. Suitable biological material can include, for example, bovine pericardium (or pericardium from other sources). The leaflets 456 can be secured to one another at their adjacent sides to form commissures 458, each of which can be secured to a respective post 404 (e.g., to a support post 407) or to the frame 402.

In the depicted example, the valvular structure 454 includes three leaflets 456, which can be arranged to collapse in a tricuspid arrangement. Each leaflet 456 can have an inflow edge portion 460. As shown in FIG. 12, the inflow edge portions 460 of the leaflets 456 can define an undulating, curved scallop edge that follows or tracks portions of the struts 412 of frame 402 in a circumferential direction when the frame 402 is in the radially expanded configuration. The inflow edges 460 of the leaflets can be referred to as a "scallop line."

As shown in FIG. 12, the inflow edge portions 460 of the leaflets 456 can be sutured to an inner skirt 464 generally along the scallop line. The inner skirt 464 can in turn be sutured to adjacent struts 412 of the frame 402, for example, via one or more sutures 462. In other examples, the leaflets 456 can be sutured directly to the frame 402 along the scallop line.

The prosthetic valve 400 can further include one or more skirts or sealing members. For example, as mentioned previously, the prosthetic valve 400 can comprise an inner skirt 464, mounted on the radially inner surface of the frame 402. The inner skirt 464 can function as a sealing member to prevent or decrease perivalvular leakage, to anchor the leaflets to the frame, and/or to protect the leaflets against damage caused by contact with the frame during crimping and during working cycles of the prosthetic valve. The prosthetic valve 400 can further include an outer skirt 466 mounted on the outer surface of the frame 402. The outer skirt 466 can function as a sealing member for the prosthetic valve by sealing against the tissue of the native valve annulus and helping to reduce paravalvular leakage past the prosthetic valve. The inner and outer skirts 464, 466 can be formed from any of various suitable biocompatible materials, including any of various synthetic materials, including fabrics (e.g., polyethylene terephthalate fabric) or natural tissue (e.g., pericardial tissue). Further details regarding the use of skirts or sealing members in prosthetic valve can be found, for example, in U.S. Patent Application No. 62/854, 702.

The prosthetic valve 400 can be radially expandable and compressible between a radially expanded configuration and a radially compressed configuration. FIG. 13 shows the bare frame 402 of prosthetic valve 400 (without the leaflets or other components) for purposes of illustrating the configuration of the frame 402. While only one side of the frame 402 is depicted in FIG. 13, it should be appreciated that the frame 402 forms an annular structure having an opposite side that is substantially identical to the portion shown.

As shown in FIG. 13, the struts 412 of frame 402 can comprise a curved shape. The struts 412 can define a plurality of first and second cells extending circumferentially around the frame 402. Each first cell 414 can have an axially-extending elliptical shape including first and second apices 416 (e.g., inflow apex 416a and outflow apex 416b) disposed at the major vertices of the ellipse. Each first cell 414 can further comprise a respective second cell 418 disposed within the outer perimeter of the first cell 414. The second cell 418 can have a circumferentially-extending elliptical shape including first and second apices 420 (e.g., inflow apex 420a and outflow apex 420b) disposed at the minor vertices of the ellipse.

In some examples, such as the example shown in FIG. 13, each strut 412 can have a recurve or S-shape including a first, upwardly curved portion 413 and a second, downwardly curved portion 415 separated by an inflection point. Curved portion 413 has a convex curved surface facing the outflow end of the frame and a concave curved surface facing the inflow end of the frame, while curved portion 415 has a concave curved surface facing the outflow end of the frame and a convex curved surface facing the inflow end of the frame. Each strut 412 can terminate at either end in an asymptotic manner against a post 404 (e.g., a support post 407 and/or an actuator mechanism 406) such that it is nearly parallel with a longitudinal axis extending through the inflow and outflow ends of the frame 402. The struts 412 can be arranged such that the upwardly curved portion 413 is disposed nearer the inflow end 408 of the frame 402 and the downwardly curved portion 415 is disposed nearer the outflow end 410.

As mentioned, the frame 402 can comprise a plurality of axially-extending struts or posts 404, including a plurality of first actuator struts or actuator posts 422 (which are lower posts in the illustrated example and can extend to the inflow end of the frame) and a plurality of second actuator struts or actuator posts 424 (which are upper posts in the illustrated example and can extend to the outflow end of the frame). Each first actuator post 422 can be axially aligned with a corresponding second actuator post 424 for a pair of first and second actuator posts. One or more pairs of actuator posts 422, 424 in combination with an actuator 426 (such as a threaded rod) can be configured as actuator mechanisms 406. The frame 402 can further comprise additional posts 404 configured as support posts 407. The support posts 407 can be disposed between each pair of adjacent circumferentially disposed first cells 414, and the actuator mechanisms 406 can be disposed such that they extend through and are coupled to the apices 416, 420 of the first and second cells. The posts 404 can be coupled together via the struts 412.

Each first cell 414 is formed by two upper struts 468a, 468b and two lower struts 470a, 470b. Each upper and lower strut 468, 470 is coupled on one end to an actuator mechanism 406 and on the other end to a support post 407. The upper struts 468a, 468b can be part of an upper row of struts that defines the outflow end of the frame and the lower struts 470a, 470b can be part of a lower row of struts that defines the inflow end of the frame. Each second cell 418 is formed by two upper struts 472a, 472b and two lower struts 474a, 474b. The lower ends of the upper struts 472a, 472b and the upper ends of the lower struts 474a, 474b can be connected to the support posts 407. The upper ends of the upper struts 472a, 472b and the lower ends of the lower struts 474a, 474b can be connected to a respective actuator mechanism 406. In the illustrated example, the upper ends of the upper struts 472a, 472b can be connected to a second post 424 and the lower ends of the lower struts 474a, 474b can be connected to a first post 422.

As mentioned, the first and second cells 414, 418 can each comprise an inflow apex 416a, 420a and an outflow apex 416b, 420b. Each pair of posts 422, 424 can extend through and be coupled to the inflow and outflow apices 416, 420 of a respective first and second cell pair. In the illustrated example, the frame 402 comprises six first cells 414 extending circumferentially in a row, with a second cell 418 within each first cell 414, and six pairs of posts 422, 424 coupled to a respective pair of cells 414, 418. However, in other examples, the frame 402 can comprise a greater or fewer number of first cells 414 within a row, and a correspondingly greater or fewer number of second cells 418 and/or pairs of posts 422, 424.

In some examples, each pair of actuator posts 422, 424 can be configured as part of an actuator mechanism 406 in combination with an actuator 426 (such as a threaded rod). For example, in the illustrated example, each of the six pairs of actuator posts 422, 424 is configured as part of an actuator mechanism 406 in combination with an actuator 426. In other examples, not all pairs of actuator posts 422, 424 need be part of actuator mechanisms. Where a pair of actuator posts 422, 424 is configured as part of an actuator mechanism, a screw/actuator bolt/threaded rod 426 (including a head portion 425) extends through each actuator post 422, 424 of the pair to effect radial compression and expansion of the frame, similar to actuator mechanisms 206 described previously. If a pair of actuator posts 422, 424 is not used as an actuator mechanism, an actuator 426 need not extend through the actuator posts 422, 424 of that pair. In the description that follows, the first and second actuator posts 422, 424, respectively, that are used as actuator mechanisms (i.e., those that include actuators 426), can be referred to as first and second actuator frame members 422, 424, or more simply, first and second frame members 422, 424.

Though in the illustrated example the actuator 426 is shown as a threaded rod, in other examples the actuator 426 can be any of various members and/or mechanisms configured to move the first and second actuator posts 422, 424 axially relative to one another to expand and/or compress the frame 402. For example, in other examples, the actuator 426 can be a linear rack comprising a plurality of teeth and can be configured to engage a corresponding pawl on the first and/or second actuator posts, or vice versa.

In the illustrated example, the actuator mechanisms 406 can function in the same manner as actuator mechanisms 206 and can comprise a threaded nut 423 disposed at an outflow end portion of the first frame member 422 configured to engage the threaded rod 426. The nut 423 can be housed in a passageway of the second frame member 422 (e.g., disposed within a window 427). As shown in FIGS. 12-13, the nut 423 can be sized to fill the window 427 such that the nut 423 is restrained from movement relative to the second frame member 422.

Rotation of the threaded rod 426 in a first direction (e.g., clockwise) can cause corresponding axial movement of the first and second frame members 422, 424 toward one another (as shown by arrows 428), expanding the frame 402, and rotation of the threaded rod 426 in a second direction (e.g., counterclockwise) causes corresponding axial movement of the first and second frame members 422, 424 away from one another (as shown by arrows 430), compressing the frame. As the frame 402 moves from a compressed configuration to an expanded configuration, the gap G (FIG. 13) between the first and second frame members 422, 424 of the actuator mechanism 406 can narrow.

The threaded rod 426 can comprise a stopper 432 (e.g., a nut) disposed thereon. The stopper 432 can be disposed on the threaded rod 426 such that it sits within the gap G. During crimping/compression of the prosthetic valve 400, the threaded rod 426 can be rotated in the second direction (e.g., counterclockwise) causing the stopper 432 to move toward the outflow end portion 434 of the frame 402 until it abuts the inflow edge of the second frame member 424.

Because the threaded rod 426 is secured to the frame 402 at axially spaced locations (the inflow end 408 and the outflow end 410) rotating the threaded rod 426 causes axial movement of the inflow end 436 and outflow end 434 relative to one another to cause radial expansion or compression of the frame 402. For example, moving the inflow and outflow ends 436, 434 toward one another causes the frame 402 to foreshorten axially and expand radially. Conversely, moving the inflow and outflow ends 436, 434 away from one another causes the frame 402 to elongate axially and compress radially.

As shown in FIG. 13, the support posts 407 can extend longitudinally and can have an inflow end portion 438 and an outflow end portion 440. The outflow end portion 440 of one or more support posts 407 can include a commissure support member 442. The commissure support member 442 can comprise first and second commissure arms 444 defining a commissure opening 446 between them. The commissure opening 446 can extend radially through a thickness of the post 404 and can be configured to accept a portion of the valvular structure 454 (e.g., the commissure 458) to couple the valvular structure 454 to the frame 402. In the illustrated example, the commissure opening 446 has a substantially rectangular shape and extends to the outflow end of the post 404. However, in other examples, the commissure opening can have any of various shapes (e.g., square, oval, square-oval, triangular, L-shaped, T-shaped, C-shaped, etc.). In some examples, the opening 446 can be fully enclosed by the post (e.g., not extending to the outflow edge) such that a portion of the valvular structure can be slid radially (rather than axially) into the commissure opening 446. The outflow end of each commissure arm 444 can include a tooth 448 extending into the commissure opening 446. The teeth 448 can help retain the commissure 458 within the commissure opening. Each commissure 458 can be mounted to a respective commissure support member 442, such as by inserting a pair of commissure tabs of adjacent leaflets through the opening 446 and suturing the commissure tabs to each other and/or the arms 444.

The inflow end portion 438 of each support post 407 can comprise a cantilevered extension 450 that extends toward the inflow end portion 436 of the frame 402. The extension 450 can comprise an aperture 452 extending radially through a thickness of the extension. In some examples, the extension 450 can extend such that an inflow edge of the extension aligns with or substantially aligns with an inflow edge of the frame 402. In use, the extension 450 can prevent or mitigate portions of the outer skirt 466 from extending radially inwardly and thereby prevent of mitigate any obstruction of flow through the inflow end 436 caused by the outer skirt 466. The extensions 450 can further serve as supports to which portions of the inner and/or outer skirts 464, 466 can be coupled. For example, sutures used to connect the inner and/or outer skirts can be wrapped around the extensions 450 and/or can extend through openings 452. In some examples, the cusp edge portions 460 of the leaflets 456 can be supported by the extensions 450, or selected ones of the extensions. For example, the cusp edge portions 460 can be secured to adjacent extensions 450 with sutures, which can extend through the openings 452.

As mentioned, FIG. 13 depicts only one side of the frame 402. Though only one support post 407 comprising a commissure support member 442 is shown in FIG. 13, it should be noted that the frame 402 can comprise any number of support posts 407, any number of which can be configured as commissure support members 442. For example, a frame 402 can comprise six support posts 407, three of which are configured as commissure support members 442. In some examples, for example, a frame can comprise one, two, three, or four commissure support members.

The actuator mechanisms 406 can be releasably coupled to one or more actuator assemblies 300, as described previously with respect to prosthetic valve 200. So coupled, the prosthetic heart valve 400 can be deployed at a selected implantation site using the same method described previously for prosthetic heart valve 200. The actuator assemblies 300 can actuate the actuator mechanisms 406 to expand and/or compress the frame 402.

Once the prosthetic valve 400 has been implanted at a selected implantation site within a patient, the patient's native anatomy (e.g., the native aortic annulus) may exert radial forces against the prosthetic valve 400 that would tend to compress the frame 402. However, the engagement of the threaded rod 426 with the threaded nut 423 of the first frame member 422 prevents such forces from compressing the frame 402, thereby ensuring that the frame remains locked in the desired radially expanded state.

If repositioning or recapture and removal of the prosthetic valve 400 is desired, the prosthetic valve can be compressed (from an expanded or partially expanded configuration) by rotating the threaded rod 426 (e.g., using driver 304 of actuator assembly 300) in a second, opposing direction. The rotation of the threaded rod 426 can cause axial movement of the first and second frame members 422, 424 of the post away from one another to increase the distance between the frame members 422, 424, causing the frame to elongate axially and compress radially. Once the prosthetic valve 400 has been recompressed it can be repositioned at the implantation site, once repositioned, the prosthetic valve 400 can be expanded as described previously. The prosthetic valve can be re-compressed, repositioned, and re-expanded multiple times, as needed. In some cases, the prosthetic valve 400 can be fully compressed and "recaptured," that is, retracted back into a sheath and/or removed from the patient's body.

Figure 14:
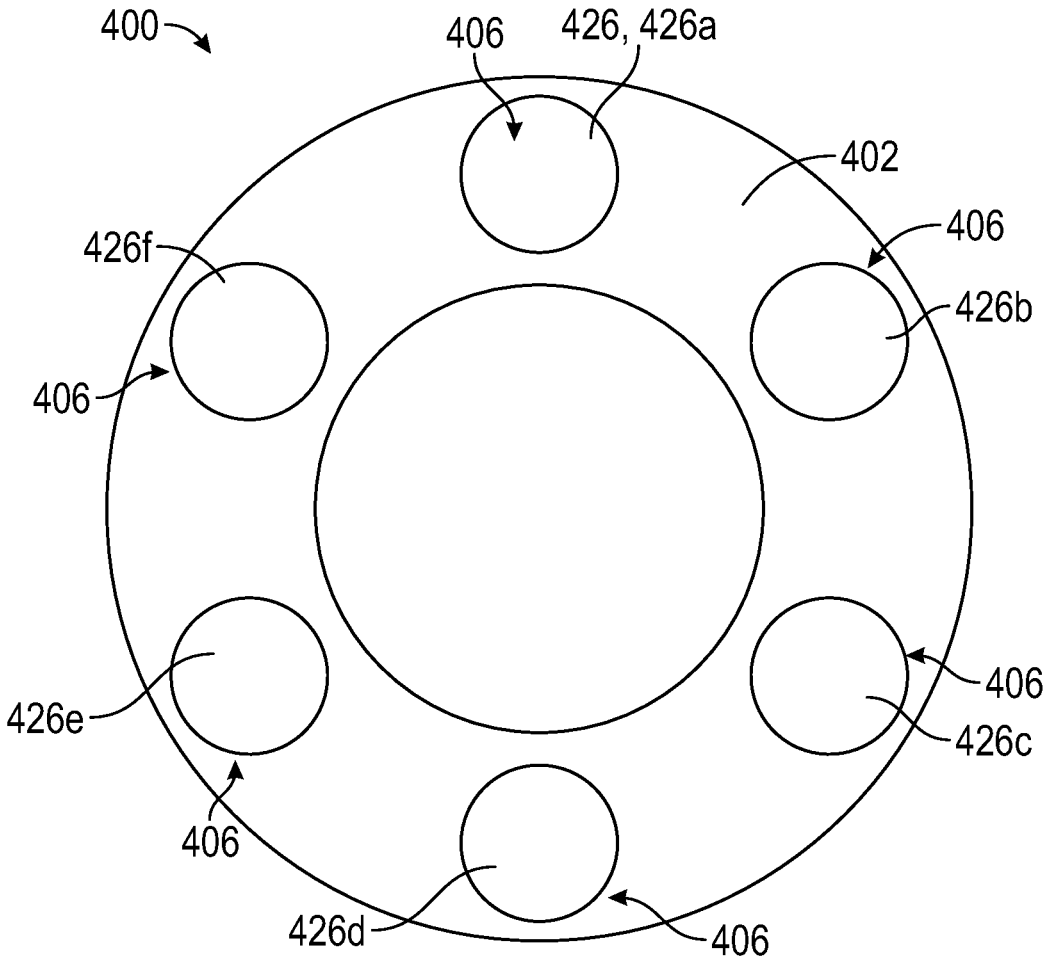
FIG. 14 is a top plan schematic view of the prosthetic heart valve of FIG. 12.

In some examples, selected threaded rods 426 can be configured as "right-hand" rods and selected threaded rods 426 can be configured as "left-hand" rods. As used herein, the term "right-hand" rod means a rod wherein rotation of the rod in a first direction (e.g., clockwise) effects expansion of the frame 402 and the term "left-hand" rod means a rod wherein rotation of the rod in a second direction (e.g., counter clockwise) effects expansion of the frame 402. Referring to FIG. 14, the prosthetic valve 400 can comprise six actuator mechanisms 406, each including a threaded rod 426 (e.g., threaded rods 426a, 426b, 426c, 426d, 426e, and 426f).

In some examples, the right-handed and left-handed rods can be disposed in an alternating pattern around the circumference of the valve 400 such that rods 426a, 426c, and 426e are configured as right-handed rods, and rods 426b, 426d, and 426f are configured as left-handed rods. During expansion of the frame 402, the right-handed rods 426a, 426c, 426e can be rotated (e.g., using a mechanism in the handle of the delivery apparatus) in a first direction (e.g., clockwise) and the left-handed rods 426b, 426d, and 426f can be rotated in a second direction (e.g., counter clockwise) opposite the first direction. During compression of the frame 402, the right handed rods 426a, 426c, 426e can be rotated in the second direction (e.g., counterclockwise) and the left-handed rods 426b, 426d, 426f can be rotated in the first direction (e.g., clockwise). The application of opposingly-directed rotational forces to alternating rods 426 can help prevent or mitigate jerking or rocking motions of the frame while the frame is expanded or compressed.

In other examples, the right-handed rods can be disposed along a first semi-circular portion of the circumference of the frame 402 and the left-handed rods can be disposed along a second semi-circular portion of the circumference, such that rods 426a, 426b, and 426c are configured as right-handed rods and rods 426d, 426e, and 426f are configured as left-handed rods. During expansion of the frame 402 the right-handed rods 426a, 426b, 426c can be rotated in a first direction (e.g., clockwise) and the left-handed rods 426d, 426e, 426f can be rotated in a second, opposing direction (e.g., counter clockwise). During compression of the frame 402, the right handed rods can be rotated in the second direction (e.g., counterclockwise) and the left-handed rods can be rotated in the first direction (e.g., clockwise).

FIGS. 15-28 illustrate another example of an actuator assembly 500 (see e.g., FIG. 22) of a delivery apparatus that can be used to expand and/or compress a prosthetic valve, for example, any of the prosthetic valves disclosed herein. The actuator assembly 500 can be a component of a delivery apparatus (such as delivery apparatus 100, described previously), and can be configured to releasably couple and actuate a respective actuator/screw/actuation bolt/threaded rod of a prosthetic valve, such as a threaded rod 504 of actuator mechanism 506, partially shown in FIG. 22-25. Though not fully shown, actuator mechanism 506 can have first and second actuator posts/frame members separated by a gap through which the threaded rod 504 extends (similar to first and second frame members 422 and 424 of prosthetic valve 400). The threaded rod 504 can be used in lieu of or in addition to threaded rods 234 and/or 426 of prosthetic valves 200 and 400. The delivery apparatus can include a plurality of actuator assemblies 500, one for each threaded rod 504 of the prosthetic valve.

Figures 15, 16, 17:
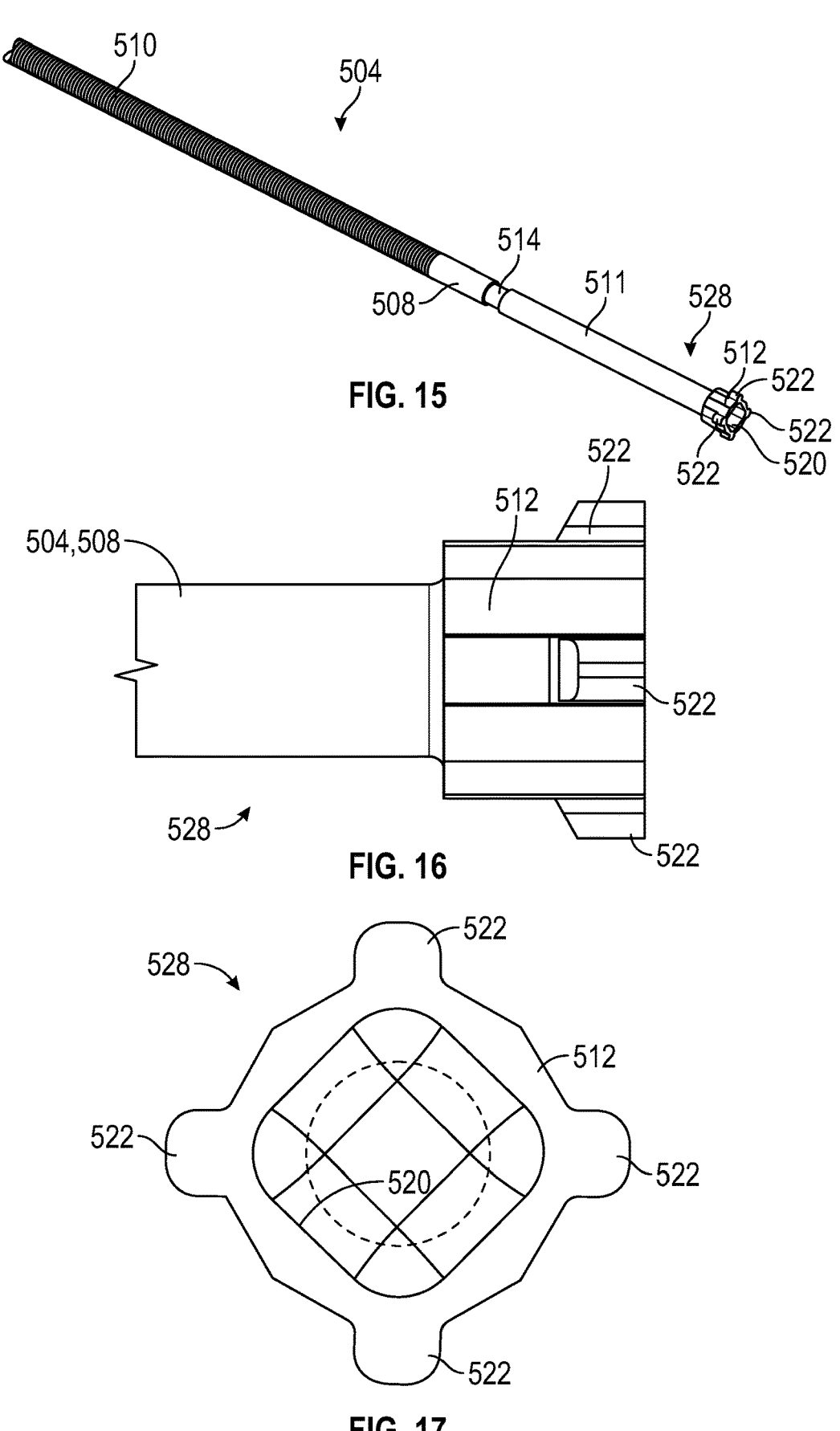
FIG. 15 is a perspective view of a threaded rod of an actuator mechanism, according to one example.
FIG. 16 is a side elevation view of a portion of the threaded rod of FIG. 15.
FIG. 17 is an end-on view of the threaded rod of FIG. 15.

Referring to FIGS. 15-17, the threaded rod 504 can comprise an elongated body 508 having a threaded portion 510, a non-threaded portion 511, and a head portion 512 configured to be releasably coupled to a respective actuator assembly 500. In some examples, such as the illustrated example, the threaded rod 504 can comprise an annular notch 514 formed in the non-threaded portion 511. In some particular examples, the notch 514 can house a stopper, such as stopper 432 described previously, which can be swaged to the rod 504. In other examples, the threaded rod 504 can be formed without a notch 514. In such examples, the stopper can be welded to the rod 504 at a selected location.

Figures 26, 27, 28:
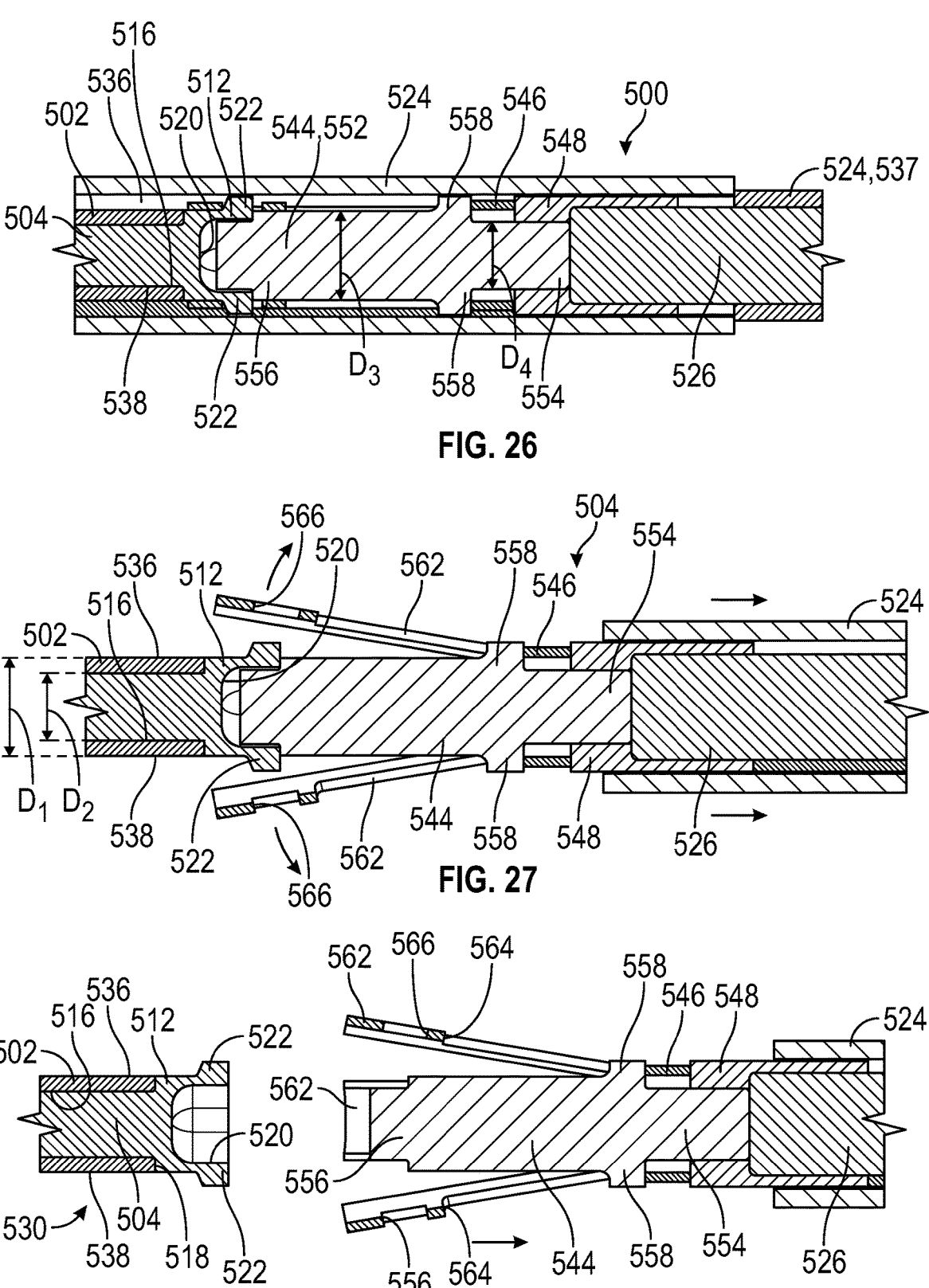
FIGS. 26-28 illustrate cross-sectional side elevation views of the exemplary method for decoupling an actuator assembly of FIGS. 22-25.

As shown in FIG. 27, the head portion 512 can have a diameter $D_1$ greater than a diameter D2 of the inner bore 516 of a frame 502 of a prosthetic valve, such that the head portion 512 is prevented from moving into the inner bore 516 of the frame 502 and such that the head portion 512 abuts the outflow edge 518 of the frame 502, e.g., as shown in FIG. 28. The head portion 512 of the threaded rod 504 can be used to apply a distally-directed force to the frame 502, for example, during radial expansion of the frame 502. The frame 502 can have the same configuration as frame 402.

The head portion 512 can comprise a central recess 520 and one or more projections 522 disposed about an outer perimeter of the head portion 512. In the illustrated example, as shown in FIG. 17, the projections 522 can comprise a substantially semi-circular shape in cross section. In other examples, the projections 522 can have any of various other shapes in cross section, such as square, rectangular, triangular, etc. Though the illustrated example shows four projections 522, in other examples the head portion 512 can have any number of projections, for example, one, two, three, four, five, six, seven, eight, etc. In the illustrated example, the central recess 520 is configured as a square recess with rounded corners, however, in other examples, the central recess 520 can have any of various other shapes, such as rectangular, ovular, triangular, etc.

Rotation of the threaded rod 504 while holding the outflow end of the frame 502 steady at a fixed location relative to the distal end portion of the delivery apparatus and the surrounding anatomy (e.g., using an actuator assembly 500 of the delivery apparatus) or applying a distally-directed force to the frame 502 causes axial movement of the inflow end and outflow end of the frame 502 relative to one another to cause radial expansion or compression of the frame. For example, moving the inflow and outflow ends toward one another causes the frame 502 to foreshorten axially and expand radially. Conversely, moving the inflow and outflow ends away from one another causes the frame 502 to elongate axially and compress radially.

Figure 18:
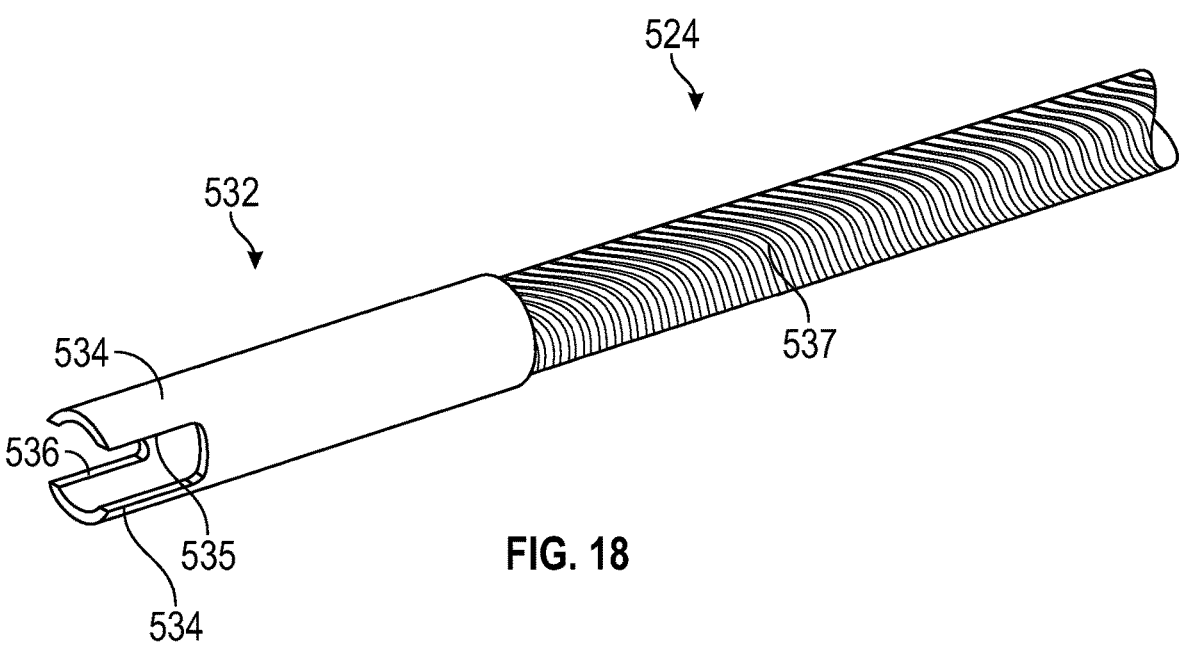
FIG. 18 is a perspective view of a portion of an outer sleeve of an actuator assembly, according to one example.
Figure 19:
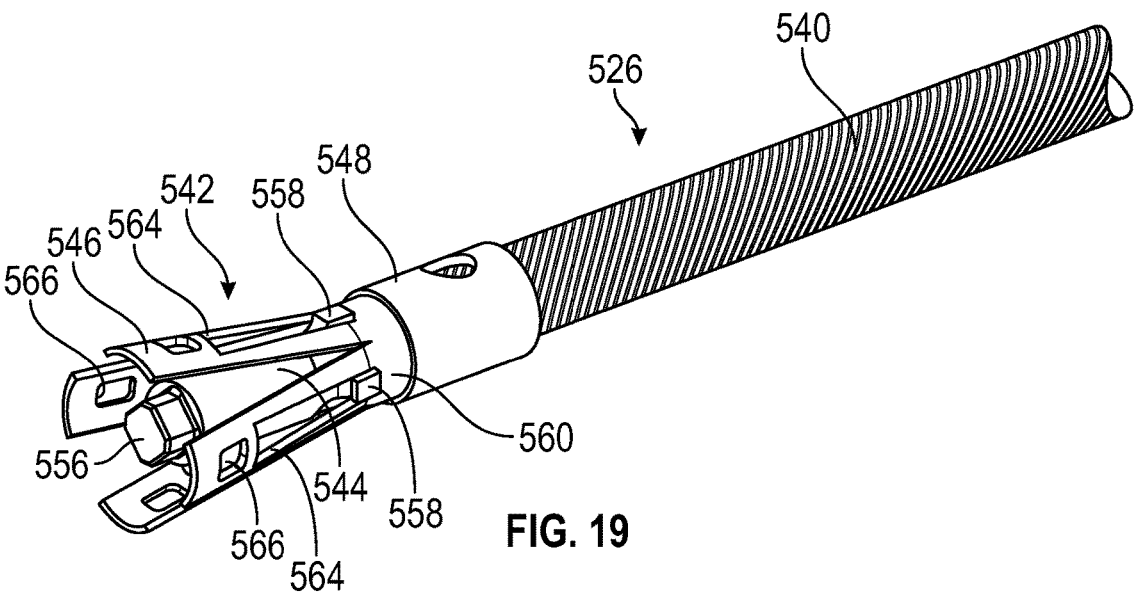
FIG. 19 is a perspective view of a portion of a driver of an actuator assembly, according to one example.

Referring to FIGS. 18-21, each actuation assembly 500 can comprise a first actuation member configured as a support tube or outer sleeve 524 (FIG. 18) and a second actuation member configured as a driver 526 (FIG. 19). As best seen in FIG. 26, the driver 526 can extend through the outer sleeve/support tube 524. The distal end portions of the outer sleeve 524 and driver 526 can be configured to engage or abut the outflow end portion 528 (FIG. 15) of the threaded rod 504 and/or the outflow end portion 530 of the frame 502. The proximal portions of the outer sleeve 524 and driver 526 can be operatively coupled to the handle of a delivery apparatus (e.g., handle 104 of delivery apparatus 100). The delivery apparatus in this example can include the same features described previously for delivery apparatus 100. In particular examples, the proximal end portions of each driver 526 can be operatively connected to the knob 112 such that rotation of the knob 112 (clockwise or counter-clockwise) causes corresponding rotation of the drivers 526. The proximal end portions of each outer sleeve 524 can be operatively connected to the knob 114 such that rotation of the knob 114 (clockwise or counterclockwise) causes corresponding axial movement of the sleeves 524 (proximally or distally) relative to the drivers 526. In other examples, the handle can include electric motors for actuating these components.

Figure 22:
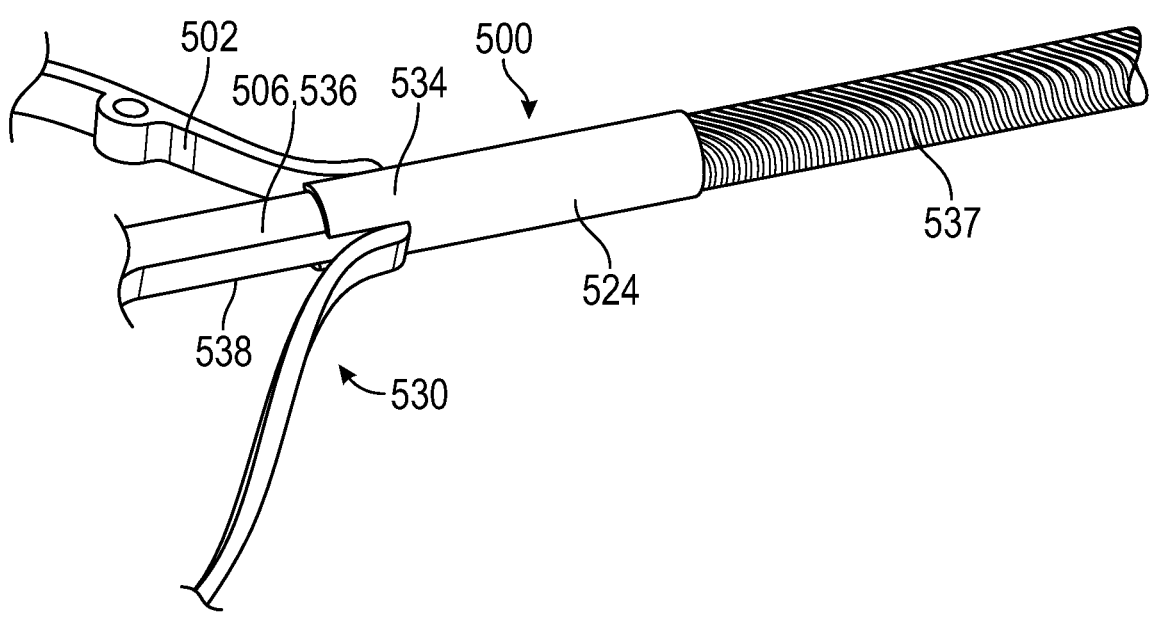
FIGS. 22-25 illustrate perspective views of an exemplary method for decoupling an actuator assembly from an actuator mechanism of a prosthetic heart valve, according to one example.

Referring to FIG. 18, a first or distal end portion 532 of the outer sleeve 524 can comprise first and second support extensions 534 defining gaps or notches 535 between them. As shown in FIG. 22, the support extensions 534 can be oriented such that, when the actuator assembly 500 is coupled to a respective actuator 506 of the frame 502, the support extensions 534 extend partially over an outflow end portion (e.g., the upper end portion) of the frame 502, such as an outflow apex or a strut portion, and in particular, over a radially outer surface 536 and a radially inner surface 538 of an outflow apex and a vertical strut extending from the apex. The engagement of the support extensions 534 with the frame 502 counter-acts rotational forces applied to the frame by the rods 504 during expansion of the frame 502. In the absence of a counter-force acting against these rotational forces, the frame tends to "jerk" or rock in the direction of rotation of the rods when they are actuated to expand the frame. The illustrated configuration is advantageous in that outer sleeves 524, when engaging the actuator mechanisms 506, can prevent or mitigate such jerking or rocking motion of the frame when the frame is expanded.

In some examples, as shown in FIG. 18, the distal end portion 532 of the outer sleeve 524 can comprise a different material and/or construction than the elongated body 537. For example, in some particular examples, the distal end portion 532 can be a laser cut tube formed comprising a nickel-cobalt base alloy, such as MP35N Alloy® and the elongated body 537 can be stainless steel. In some particular examples, the elongated body 537 can be a hollow, torque cable. In other examples, the elongated body 537 can be a laser cut slotted hypotube.

Referring to FIG. 19, the driver 526 can comprise an elongated body 540, and an engagement portion 542 disposed at a distal end portion of the elongated body 540. In some particular examples, the elongated body 540 can comprise a cable, for example, a 0.85 mm cable. In other examples, the elongated body 540 can be, for example, a slotted hypotube. The engagement portion 542 can comprise a driver head 544 and a gripper member 546. As shown in the illustrated example, the driver head 544 can be coupled to the elongated body using, for example, a fastener 548. In other examples, the driver head 544 can be welded or otherwise permanently coupled to the elongated body 540. In still other examples, the driver head 544 and the elongated body 540 can be formed integrally with one another.

In some examples, the gripper member 546 can be coupled to the elongated body 540 by sandwiching the annular base 560 of the gripper member 546 between the second end portion 554 of the driver head 544 and the fastener 548. The fastener 548 can then be welded to the driver head 544, capturing the annular base 560 between them such that the gripper member is restrained from axial movement relative to the driver head 544. In other examples, the gripper member 546 can be formed integrally with the fastener 548, or otherwise can be coupled to the fastener 548 such as via welding. In some particular examples, the elongated body 540, driver head 544, and gripper member 546 can be welded together, in other examples, they can be coupled together using a swaged coupling.

Figure 20:
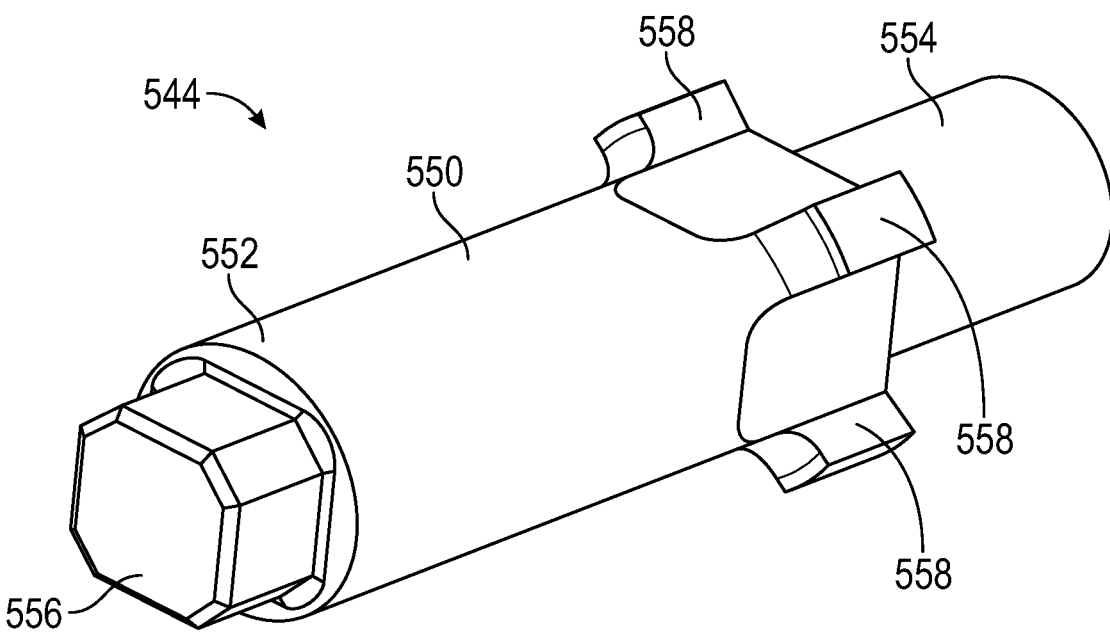
FIG. 20 is a perspective view of the driver head of the driver of FIG. 19.

Referring to FIG. 20, the driver head 544 can comprise a main body 550 having a first end portion 552 and a second end portion 554, an engagement member 556, and one or more extension members/projections 558. The one or more projections 558 can extend radially outwardly from the main body 550 and can be spaced apart from one another around a perimeter of the driver head 544. The engagement member 556 can extend distally from the first end portion 552 of the main body 550 and can be configured to engage the recess 520 of a respective threaded rod 504. Though in the illustrated example the engagement member 556 has a square shape with chamfered edges in cross-section, in other examples, the engagement member 556 can have any of various shapes, for example, rectangular, triangular, ovular, etc. The recess 520 in the head portion 512 of the threaded rod 504 can be correspondingly shaped to receive the engagement member 556. The shape of the engagement member 556 and the corresponding recess 520 can advantageously improve torque transmission from the driver 526 to the threaded rod 504.

As best seen in FIG. 26, the first end portion 552 of the driver head 544 can have a first diameter $D_3$ and the second end portion 554 can have a second, smaller diameter $D_4$. The second end portion 554 can extend into the fastener 548 to couple the driver head 544 to the elongated body 540. In some particular examples, the driver head 544 can comprise a nickel-cobalt base alloy, such as MP35N Alloy®.

Figure 21:
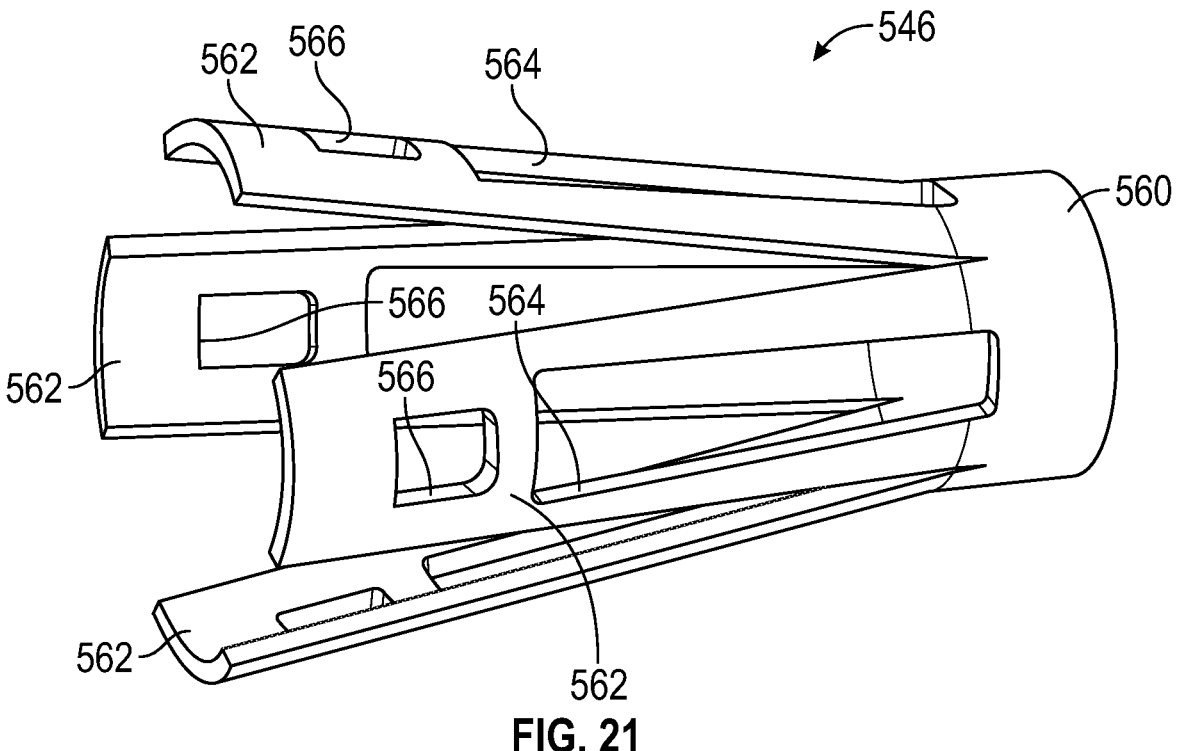
FIG. 21 is a perspective view of the gripper member of the driver of FIG. 19.
Figure 23:
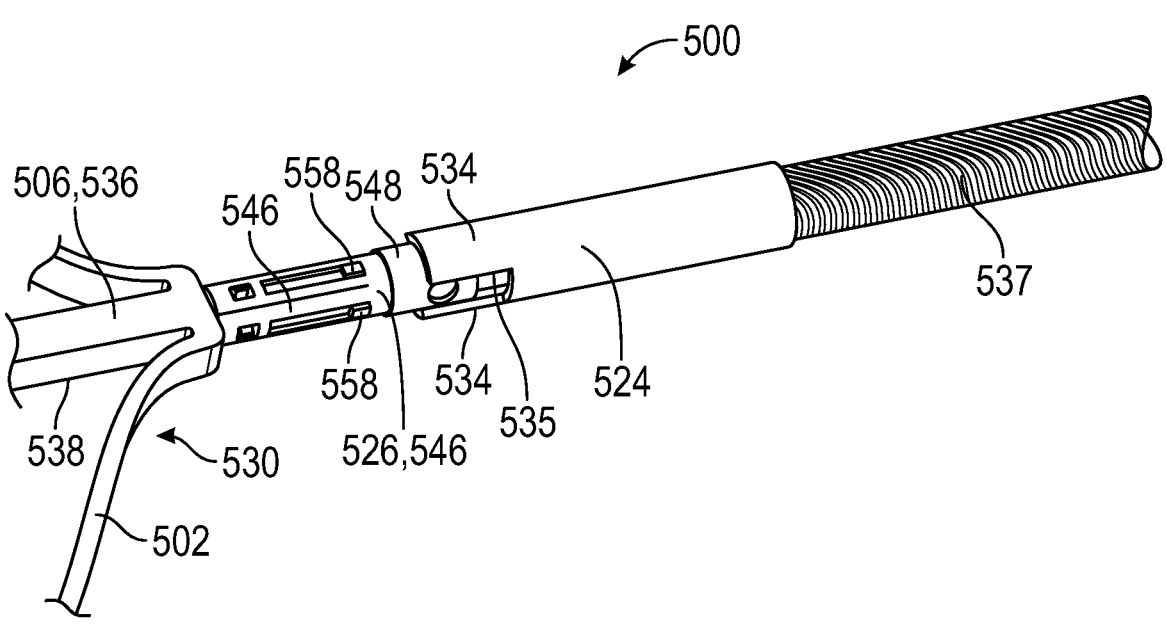

Referring now to FIG. 21, the gripper member 546 can comprise an annular base member 560 and one or more extension members/wings/arms 562. The arms 562 can extend distally from the base member 560 and can be resilient such that they are movable between an expanded position (FIG. 19) and a compressed position (FIG. 23). The arms 562 can be configured to bias radially outwardly (e.g., away from longitudinal axis of the driver 526) into the expanded shape, for example, by shape setting the arms 562. Each arm 562 can comprise a first, elongated opening 564 and a second opening 566. In the illustrated example, the gripper member 546 comprises four arms, however, in other examples the gripper member 546 can comprise any number of arms, for example, one, two, three, four, five, six, seven, eight, etc. In some particular examples, the gripper member 546 can comprise a laser-cut Nitinol tube, which can be heat-set such that the arms 562 bias radially outwardly.

As shown in FIG. 19, the projections 558 of the driver head 544 can extend into the first openings 564 to restrain the gripper member 546 against axial and rotational movement relative to the driver head 544. The second openings 566 can be configured (e.g., sized and shaped) to engage the projections 522 disposed on the head portion 512 of a respective threaded rod 504, thereby releasably coupling the actuation assembly 500 to the threaded rod 504. In the illustrated example, the first opening 564 is an elongated, rectangular opening and the second opening 566 is a substantially square opening, however, in other examples, the openings 564, 566 can have any of various shapes corresponding to the shape and size of the projections 558 of the driver head 544 and the projections 522 of the threaded rod 504, respectively.

The actuator assembly 500 can couple a respective actuator mechanism 506 of a prosthetic valve as follows. The engagement member 556 of the driver 526 can be disposed within the recess 520 of the head portion 512 of a threaded rod 504 such that the second openings 566 of the gripper member arms 562 are disposed adjacent the projections 522. As the outer sleeve 524 is advanced (e.g., distally) over the driver 526, the arms 562 are radially compressed until the projections 522 sit within the second openings 566, thereby coupling the actuator assembly 500 to the threaded rod 504 (e.g., as shown in FIG. 26). The outer sleeve 524 can continue to be advanced until the support extensions 534 engage the radially inner and outer surfaces 536, 538 of the frame 502, as shown in FIG. 22. So coupled, the driver 526 can be rotated (e.g., using the handle of the delivery apparatus 100) to cause corresponding rotation of the threaded rod 504. The engagement between the actuator assembly 500 and the threaded rod 504 can advantageously improve torque transfer between the driver and the threaded rod 504.

Generally, the prosthetic valve is placed in a radially compressed state and the actuator mechanisms 506 of the prosthetic valve are releasably coupled to one or more actuator assemblies 500 in the manner described previously, as shown in FIGS. 22 and 26. The delivery apparatus and the prosthetic valve can be advanced over a guidewire through the vasculature of a patient to a selected implantation site (e.g., the native aortic annulus). For example, when implanting the prosthetic valve within the native aortic valve, the delivery apparatus and the prosthetic valve can be inserted into and through a femoral artery, and through the aorta to the native aortic valve. The prosthetic valve can then be deployed at the implantation site (e.g., within the native aortic valve) and can be expanded and locked in the expanded configuration using the actuator mechanisms 506.

To deploy the prosthetic valve, the physician can actuate the actuator mechanisms 506 by rotating the drivers 526 in a first direction (e.g., by rotating the knob 112 or actuating a motor), which causes corresponding rotation of the threaded rods 504. The rotation of the threaded rod 504 in the first direction causes axial movement of the first and second frame members of the actuator mechanism (e.g., similar to first and second frame members 422, 424 of prosthetic valve 400) toward one another, causing the frame 502 to foreshorten axially and expand radially until a selected diameter is achieved. The disclosed actuator mechanism examples advantageously allow for continuous prosthetic valve expansion (e.g., without the stepped expansion that results from a ratcheting mechanism) and allow the prosthetic heart valve to be deployed at any of various diameters.

Figure 24:
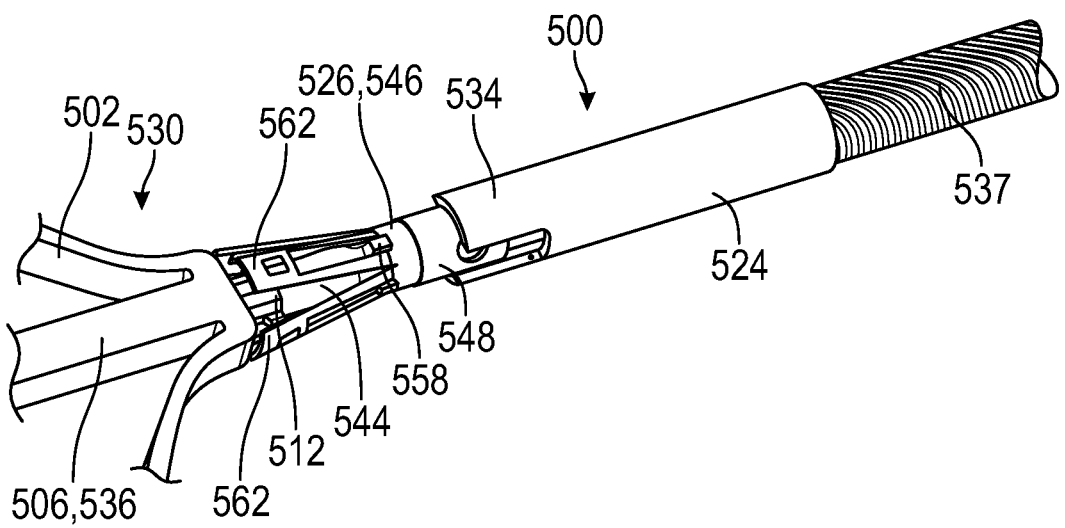
Figure 25:
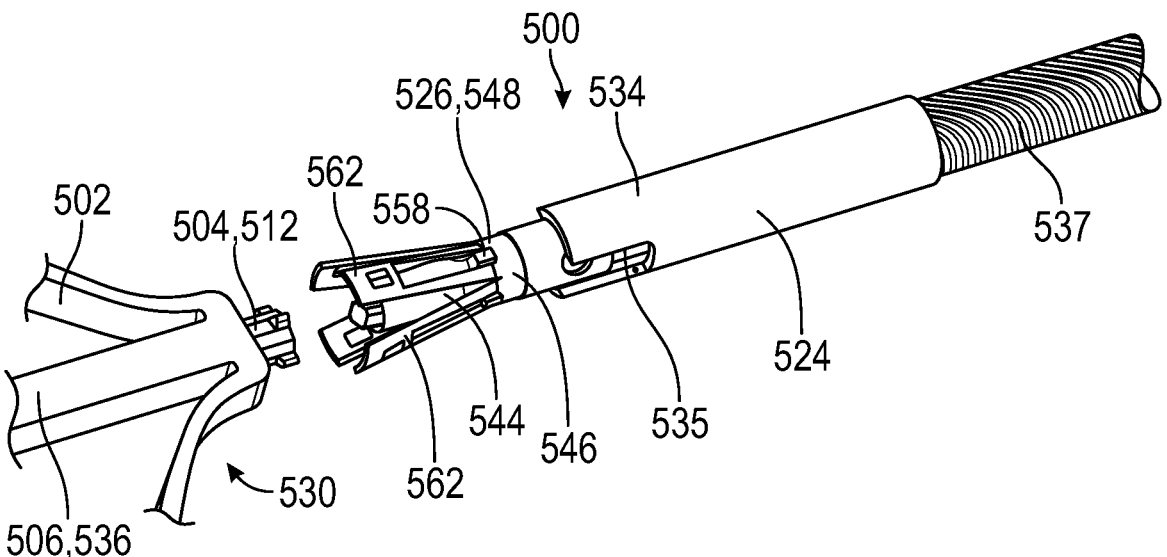

Referring to FIGS. 22-28, once final positioning and expansion of the prosthetic valve is achieved, the actuator assemblies 500 can be released from the prosthetic valve in the following exemplary manner. The outer sleeve 524 can be retracted to uncover the connection between the driver 526 and the threaded rod 504, as shown in FIGS. 23 and 27. This can be achieved by rotating the knob 114 or actuating a motor in the handle of the delivery apparatus 100. As shown in FIGS. 24 and 27, once the outer sleeve 524 is retracted, the arms 562 of the gripper member 546 can expand radially outwardly away from the head portion 512 of the threaded rod 504. As shown in FIGS. 25 and 28, the driver 526 can then be retracted, removing the engagement member 556 from within the recess 520 of the rod 504, thereby decoupling the driver 526 from the rod 504. At this stage, the delivery apparatus (including the actuator assemblies 500) can be retracted relative to the prosthetic valve and removed from the patient's body.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An assembly, comprising:
a prosthetic heart valve comprising:
 a radially expandable and compressible frame having an inflow end portion, an outflow end portion, and a plurality of actuator mechanisms, each actuator mechanism comprising:
 a first frame member having a first inner bore and a second frame member having a second inner bore, the first and second frame members being spaced apart axially from one another, and
 an actuator having an external threaded surface and extending through the first and second inner bores; and
a delivery apparatus comprising:
 a handle,
 one or more actuator assemblies extending from the handle, each actuator assembly comprising:
 a first actuation member having a distal end portion releasably coupled to the outflow end portion of the frame, the distal end portion comprising first and second support extensions; and
 a second actuation member extending through the first actuation member and comprising a distal end portion having an engagement portion releasably coupled to the rod;
 wherein rotation of the second actuation member in a first direction causes corresponding rotation of the rod such that the first and second members move axially toward one another to expand the prosthetic valve; and
 wherein the first and second support extensions inhibit rotation of the frame relative to the one or more actuator assemblies during expansion of the prosthetic valve.

Example 2. The assembly of any example herein, particularly example 1, wherein the first support extension extends partially over a radially inner surface of the frame and the second support extension extends partially over a radially outer surface of the frame.

Example 3. The assembly of any of any example herein, particularly any one of examples 1-2, wherein a proximal end portion of the actuator comprises first and second protrusions defining a slot between them.

Example 4. The assembly of any example herein, particularly example 3, wherein the engagement portion comprises a central protrusion extending into the slot.

Example 5. The assembly of any example herein, particularly example 4, wherein the central protrusion is sized such that it does not contact an inner surface of the first actuation member.

Example 6. The assembly of any example herein, particularly any one of examples 1-5, wherein the proximal end portion of the actuator comprises one or more shoulders extending radially from a surface of the actuator.

Example 7. The assembly of any example herein, particularly example 6, wherein the engagement portion comprises one or more flexible elongated elements releasably coupled to the shoulders.

Example 8. The assembly of any example herein, particularly example 7, wherein each elongated element comprises a protrusion extending radially inwardly toward a longitudinal axis of the second actuation member.

Example 9. The assembly of any example herein, particularly example 7, wherein the one or more elongated elements bias radially outwardly from a longitudinal axis of the second actuation member.

Example 10. The assembly of any example herein, particularly any one of examples 1-9, wherein rotation of the second actuation member in a second direction causes corresponding rotation of the actuator such that the first and second frame members move axially away from one another to radially compress the prosthetic valve.

Example 11. The assembly of any example herein, particularly any one of examples 1-10, each actuator comprising a stopper disposed axially between the first and second frame members, the stopper configured to selectively abut an inflow end portion of the second frame member to prevent over crimping of the frame.

Example 12. The assembly of any example herein, particularly any one of examples 1-11, each first frame member comprising a nut disposed at an outflow end portion of the first frame member, the nut comprising an inner threaded bore configured to engage the external threaded surface of the actuator.

Example 13. The assembly of any example herein, particularly example 12, wherein the nut is visible through a window extending through a wall of the first member.

Example 14. The assembly of any example herein, particularly any one of examples 1-13, the frame comprising a plurality of circumferentially disposed hexagonal cells.

Example 15. The assembly of any example herein, particularly example 14, wherein each hexagonal cell comprises a diamond cell disposed within an outer perimeter of the hexagonal cell.

Example 16. The assembly of any example herein, particularly example 15, wherein each hexagonal cell and diamond cell comprises an inflow apex and an outflow apex, and wherein each actuator extends through the inflow and outflow apices.

Example 17. The assembly of any example herein, particularly any one of examples 1-16, wherein the frame further comprises one or more axially extending support posts.

Example 18. The assembly of any example herein, particularly any one of examples 1-17, wherein the plurality of actuator mechanisms are each coupled to one or more support posts by a plurality of struts.

Example 19. The assembly of any example herein, particularly example 18, wherein the struts are curved.

Example 20. The assembly of any example herein, particularly any one of examples 18-19, wherein each strut has a recurve shape including a first portion and a second portion separated by an inflection point.

Example 21. The assembly of any example herein, particularly example 20, wherein the first portion is an upwardly curved portion, and the second portion is a downwardly curved portion.

Example 22. The assembly of any example herein, particularly any one of examples 18-21, wherein each strut comprises a first end portion and a second end portion and wherein the first and second end portions terminate asymptotically against at least one of a respective support post and actuator mechanism.

Example 23. The assembly of any example herein, particularly any one of examples 1-22, wherein each actuator is configured as at least one of a right-handed rod and a left-handed rod.

Example 24. The assembly of any example herein, particularly example 23, wherein the prosthetic heart valve comprises six actuator mechanisms and wherein the actuators of the actuator mechanisms alternate between right-handed rods and left-handed rods about the circumference of the frame.

Example 25. An assembly, comprising:

a prosthetic heart valve comprising:

a radially expandable and compressible frame having an inflow end portion and an outflow end portion, the frame comprising a plurality of actuation mechanisms, each actuation mechanism comprising:

a first frame member having a first inner bore and a second frame member having a second inner bore, the first and second frame members being spaced apart axially from one another, and a rod having an external threaded surface and extending through the first and second inner bores, a proximal end portion of the rod comprising first and second protrusions defining a slot between them, and first and second shoulders; and a delivery apparatus comprising:

a handle, one or more actuator assemblies extending from the handle, each actuator assembly comprising:

a first actuation member having a distal end portion abutting the outflow end portion of the frame, and a second actuation member extending through the first actuation member, the second actuation member comprising a distal end portion having a central protrusion extending into the slot and first and second flexible elongated elements releasably coupled to the shoulders; and wherein rotation of the second actuation member in a first direction causes corresponding rotation of the rod such that the first and second frame members move axially toward one another to expand the prosthetic valve.

Example 26. The assembly of any example herein, particularly example 25, wherein the first actuation member further comprises first and second support extensions configured to inhibit rotation of the frame relative to the first actuation member during expansion of the frame.

Example 27. The assembly of any example herein, particularly example 26, wherein the first support extension extends partially over a radially inner surface of the frame and the second support extension extends partially over a radially outer surface of the frame.

Example 28. The assembly of any example herein, particularly any one of examples 25-27, wherein the central protrusion is sized such that it does not contact an inner surface of the first actuation member.

Example 29. The assembly of any example herein, particularly any one of examples 25-28, wherein each elongated element comprises a radially inwardly extending protrusion.

Example 30. The assembly of any example herein, particularly example 29, wherein the one or more elongated elements bias radially outwardly from a longitudinal axis of the second actuation member.

Example 31. The assembly of any example herein, particularly any one of examples 25-30, wherein rotation of the second actuation member in a second direction causes corresponding rotation of the rod such that the first and second frame members move axially away from one another to radially compress the prosthetic valve.

Example 32. The assembly of any example herein, particularly any one of examples 25-31, each rod comprising a stopper disposed between the first and second frame members, the stopper configured to selectively abut an inflow end portion of the second frame member to prevent over crimping of the frame.

Example 33. The assembly of any example herein, particularly any one of examples 25-32, each first frame member comprising a nut disposed at an outflow end portion of the first member, the nut comprising an inner threaded bore configured to engage the threaded rod.

Example 34. The assembly of any example herein, particularly example 33, wherein the nut is visible through a window extending through a wall of the first frame member.

Example 35. The assembly of any example herein, particularly any one of examples 25-34, further comprising a plurality of posts;
    wherein one or more of the posts are configured as the actuation mechanisms; and
    wherein the plurality of posts are coupled to one another by a plurality of struts.

Example 36. The assembly of any example herein, particularly example 35, wherein the struts are curved.

Example 37. The assembly of any example herein, particularly any one of examples 25-26, wherein each strut has a recurve shape including a first portion and a second portion separated by an inflection point.

Example 38. The assembly of any example herein, particularly example 37, wherein the first portion is an upwardly curved portion and the second portion is a downwardly curved portion.

Example 39. The assembly of any example herein, particularly any one of examples 25-38, wherein each strut comprises a first end portion and a second end portion and wherein the first and second end portions terminate asymptotically against respective posts.

Example 40. A delivery apparatus, comprising:
    a handle,
    one or more actuator assemblies extending from the handle, each actuator assembly comprising:
    a first actuation member having a distal end portion configured to abut an outflow end portion of a prosthetic heart valve, the distal end portion comprising first and second support extensions; and
    a second actuation member extending through the first actuation member and having a distal end portion configured to releasably couple an actuator of the prosthetic heart valve;
    wherein rotation of the second actuation member in a first direction radially expands the prosthetic valve and rotation of the second actuation member in a second direction radially compresses the prosthetic valve; and
    wherein the first support extension is configured to extend partially over a radially inner surface of the prosthetic valve and the second support extension is configured to extend partially over a radially outer surface of the prosthetic valve to inhibit rotation of the frame of the prosthetic valve relative to the actuator assemblies.

Example 41. The delivery apparatus of any example herein, particularly example 40, wherein the second actuation member comprises a central protrusion.

Example 42. The delivery apparatus of any example herein, particularly example 41, wherein the central protrusion is sized such that it does not contact an inner surface of the first actuation member.

Example 43. The delivery apparatus of any example herein, particularly any one of examples 40-42, wherein the distal end portion of the second actuation member comprises one or more flexible elongated elements.

Example 44. The delivery apparatus of any example herein, particularly example 43, wherein each elongated element comprises a protrusion extending radially inwardly toward a longitudinal axis of the second actuation member.

Example 45. The delivery apparatus of any example herein, particularly example 44, wherein the one or more elongated elements bias radially outwardly from a longitudinal axis of the second actuation member.

Example 46. An implantable prosthetic device, comprising:
    a radially expandable and compressible frame having an inflow end portion and an outflow end portion, the frame comprising:
        a plurality of posts, one or more of which are configured as actuation mechanisms comprising:
            a first frame member having a first inner bore,
            a second frame member having a second inner bore, the first and second frame members being spaced apart axially from one another, and
            an actuator having an external threaded surface and extending through the first and second inner bores, a proximal end portion of the actuator comprising first and second protrusions defining a slot between them, and first and second shoulders extending radially from an outer surface of the actuator; and
    a plurality of struts coupling adjacent posts to one another; and
    wherein rotation of the actuator in a first direction results in axial movement of the first and second frame members toward one another to radially expand the prosthetic device.

Example 47. The prosthetic device of any example herein, particularly example 46, further comprising a valvular structure comprising a plurality of leaflets disposed within the frame.

Example 48. The prosthetic device of any example herein, particularly any one of examples 46-47, wherein rotation of the actuator in a second direction results in axial movement of the first and second members away from one another to radially compress the prosthetic device.

Example 49. The prosthetic device of any example herein, particularly any one of examples 46-48, each actuator comprising a stopper disposed axially between the first and second frame members, the stopper configured to selectively abut an inflow end portion of the second frame member to prevent over crimping of the frame.

Example 50. The prosthetic device of any example herein, particularly any one of examples 46-49, each first frame member comprising a nut disposed at an outflow end portion of the first frame member, the nut comprising an inner threaded bore configured to engage the external threaded surface of the rod.

Example 51. The any example herein, particularly example 50, wherein the nut is visible through a window extending through a wall of the first frame member.

Example 52. The prosthetic device of any example herein, particularly any one of examples 46-51, the struts and posts defining a plurality of circumferentially disposed hexagonal cells.

Example 53. The prosthetic device of any example herein, particularly example 52, wherein each hexagonal cell comprises a diamond cell disposed within an outer perimeter of the hexagonal cell.

Example 54. The prosthetic device of example 53, wherein each hexagonal cell and diamond cell comprises an inflow apex and an outflow apex, and wherein each actuation mechanism extends through the inflow and outflow apices.

Example 55. The prosthetic device of any example herein, particularly any one of examples 46-54, wherein the struts are curved.

Example 56. The prosthetic device of any example herein, particularly any one of examples 46-55, wherein each strut has a recurve shape including a first portion and a second portion separated by an inflection point.

Example 57. The prosthetic device of any example herein, particularly example 56, wherein the first portion is an upwardly curved portion and the second portion is a downwardly curved portion.

Example 58. The prosthetic device of any example herein, particularly any one of examples 46-57, wherein each strut comprises a first end portion and a second end portion and wherein the first and second end portions terminate asymptotically against respective posts.

Example 59. A method, comprising:

inserting a distal end of a delivery apparatus into the vasculature of a patient, the delivery apparatus releasably coupled to a prosthetic valve via a plurality of actuator assemblies, the prosthetic heart valve including a frame comprising a plurality of actuation mechanisms each comprising a first frame member, a second frame member axially spaced from the first frame member, and an actuator extending through the first and second frame members, each actuator assembly comprising a first actuation member engaging an outflow end of the prosthetic valve and a second actuation member extending through the first actuation member and engaging an outflow end of the actuator, the first actuation member comprising a first support extension extending partially over a radially inner surface of the frame and a second support extension extending partially over a radially over surface of the frame;

advancing the prosthetic valve to a selected implantation site; and rotating the second actuation member to cause corresponding rotation of the actuator resulting in axial movement of the first and second frame members toward one another to radially expand the prosthetic valve, the first and second support extensions inhibiting rotation of the frame relative to the first actuation member during expansion.

Example 60. The method of any example herein, particularly example 59, further comprising:

rotating the second actuation member in a second direction to cause corresponding rotation of the actuator resulting in axial movement of the first and second frame members away from one another to radially compress the prosthetic valve, the first and second support extensions inhibiting rotation of the frame relative to the first actuation member during compression of the frame.

Example 61. The method of any example herein, particularly any one of examples 59-60, wherein the actuator comprises a stopper disposed between the first and second frame members, and wherein during radial compression of the frame the stopper selectively abuts an inflow end of the second frame member.

Example 62. An assembly, comprising:

a prosthetic heart valve comprising:

a radially expandable and compressible frame having an inflow end portion and an outflow end portion, and one or more actuators having an external threaded surface and configured to radially expand the frame upon rotation of the one or more actuators; and a delivery apparatus comprising:

a handle, one or more actuator assemblies extending from the handle, each actuator assembly comprising:

a first actuation member having a distal end portion releasably coupled to the outflow end portion of the frame, the distal end portion comprising first and second support extensions; and a second actuation member extending through the first actuation member and comprising a distal end portion having an engagement portion, the engagement portion comprising:

a driver head having an engagement member that extends into a corresponding recess in a corresponding actuator, and a gripper member comprising one or more arms releasably coupled to one or more projections extending from the actuator;

wherein rotation of the second actuation member in a first direction causes corresponding rotation of the actuator to expand the prosthetic valve; and wherein the first and second support extensions inhibit rotation of the frame relative to the one or more actuator assemblies during expansion of the prosthetic valve.

Example 63. The assembly of any example herein, particularly example 62, wherein the first support extension extends partially over a radially inner surface of the frame and the second support extension extends partially over a radially outer surface of the frame.

Example 64. The assembly of any example herein, particularly any one of examples 62-63, wherein the engagement portion comprises a square shape with chamfered corners in cross-section.

Example 65. The assembly of any example herein, particularly example 64, wherein the engagement member extends distally from the driver head.

Example 66. The assembly of any example herein, particularly any one of examples 62-65, wherein the engagement portion is sized such that it does not contact an inner surface of the first actuation member.

Example 67. The assembly of any example herein, particularly any one of examples 62-66, wherein the arms are movable between an expanded position and a compressed position.

Example 68. The assembly of any example herein, particularly example 67, wherein the arms bias radially outwardly from a longitudinal axis of the second actuation member.

Example 69. The assembly of any example herein, particularly any one of examples 62-68, wherein each arm comprises an opening, and wherein a respective projection of the actuator is selectively disposed within the opening.

Example 70. The assembly of any example herein, particularly any one of examples 62-69, wherein rotation of the second actuation member in a second direction causes corresponding rotation of the actuator to radially compress the prosthetic valve.

Example 71. The assembly of any example herein, particularly any one of examples 62-70 wherein the frame comprises one or more pairs of axially spaced first and second frame members, each actuator extending through the first and second frame members of a corresponding pair.

Example 72. The assembly of any example herein, particularly example 71, wherein each actuator comprises a stopper disposed axially between the first and second frame members of a corresponding pair, the stopper configured to selectively abut an inflow end portion of the second frame member.

Example 73. The assembly of any example herein, particularly any one of examples 71-72, wherein each first frame member comprises a nut disposed at an outflow end portion of the first frame member, the nut comprising an inner threaded bore configured to engage a corresponding actuator.

Example 74. A delivery apparatus, comprising:

a handle;

one or more actuator assemblies extending from the handle, each actuator assembly comprising:

a first actuation member having a distal end portion configured to abut an end portion of a prosthetic heart valve, the distal end portion comprising first and second support extensions, a second actuation member extending through the first actuation member and comprising a driver head having an engagement member configured to engage a corresponding engagement portion of an actuator of the prosthetic heart valve, and a gripper member comprising one or more arms configured to releasably couple the actuator; and wherein rotation of the second actuation member in a first direction is configured to radially expand the prosthetic valve and rotation of the second actuation member in a second direction is configured to radially compresses the prosthetic valve.

Example 75. The delivery apparatus of any example herein, particularly example 74, wherein the first support extension is configured to extend partially over a radially inner surface of the prosthetic valve and the second support extension is configured to extend partially over a radially outer surface of the prosthetic valve to inhibit rotation of the frame of the prosthetic valve relative to the actuator assemblies.

Example 76. The delivery apparatus of any example herein, particularly any one of examples 74-75, wherein the engagement portion comprises a square shape with chamfered corners in cross-section.

Example 77. The delivery apparatus of any example herein, particularly example 76, wherein the engagement member extends distally from the driver head.

Example 78. The delivery apparatus of any example herein, particularly any one of examples 74-77, wherein the second actuation member is sized such that it does not contact an inner surface of the first actuation member.

Example 79. The delivery apparatus of any example herein, particularly, any one of examples 74-78, wherein the one or more arms comprise a plurality of arms.

Example 80. The delivery apparatus of any example herein, particularly example 79, wherein the arms are movable between an expanded position and a compressed position.

Example 81. The delivery apparatus of any example herein, particularly example 80, wherein the arms bias radially outwardly from a longitudinal axis of the second actuation member.

Example 82. The delivery apparatus of any example herein, particularly any one of examples 74-81, wherein each arm comprises an opening configured to selectively couple a respective projection of the actuator.

Example 83. The delivery apparatus of any example herein, particularly any one of examples 74-82, wherein rotation of the second actuation member in a second direction is configured to cause corresponding rotation of a corresponding actuator to radially compress the prosthetic valve.

Example 84. A prosthetic heart valve comprising:

a radially expandable and compressible frame comprising:

a plurality of circumferentially spaced, axially extending posts;

a plurality of circumferentially spaced, pairs of axially extending frame members, wherein each pair of frame members includes an axially extending proximal frame member and an axially extending distal frame member that is axially spaced from the proximal frame member to define a gap therebetween, wherein each pair of frame members is positioned circumferentially between two posts;

a plurality of connecting struts coupling the posts to the proximal and distal frame members, wherein each post is connected to (i) an adjacent distal frame member of a first adjacent pair of frame members by two connecting struts, (ii) an adjacent proximal frame member of the first adjacent pair by two connecting struts, (iii) an adjacent distal frame member of a second adjacent pair of frame members by two connecting struts, and (iv) an adjacent proximal frame member of the second adjacent pair by two connecting struts, wherein each connecting strut has a concave curved portion and a convex curved portion separated by an inflection point;

a plurality of actuators extending through respective pairs of first and second frame members, wherein the actuators are configured to radially expand the frame from a radially compressed state to a radially expanded state; and a valvular structure disposed within the frame and configured to regulate the flow of blood through the frame in one direction.

Example 85. The prosthetic heart valve of any example herein, particularly example 84, wherein the struts, the posts, and the proximal and distal frame members are arranged to form a plurality of hexagonal cells and a plurality of diamond-shaped cells, wherein each diamond-shaped cell disposed within one of the hexagonal cells.

Example 86. The prosthetic heart valve of any example herein, particularly example 85, wherein each diamond-shaped cell is centered within a respective hexagonal cell.

Example 87. The prosthetic heart valve of any example herein, particularly any one of examples 85-86, wherein each hexagonal cell defines an inflow apex of the frame and an outflow apex of the frame.

Example 88. The prosthetic heart valve of any example herein, particularly any one of examples 85-87, wherein there are exactly six hexagonal cells and exactly six diamond-shaped cells.

Example 89. The prosthetic heart valve of any example herein, particularly any one of examples 85-88, wherein the hexagonal cells extend the entire length of the frame.

Example 90. The prosthetic heart valve of any example herein, particularly any one of examples 84-89, wherein the valvular structure comprises a plurality of leaflets, each leaflet comprising two commissure tabs on opposite sides of the leaflet, wherein each commissure tab is paired with an adjacent commissure tab of an adjacent leaflet to form a commissure, wherein each commissure is secured to an adjacent post.

Example 91. The prosthetic heart valve of any example herein, particularly example 90, wherein each post that is adjacent a commissure comprises a slot and a pair of commissure tabs of the adjacent commissure extends through the slot.

Example 92. The prosthetic heart valve of any example herein, particularly any one of examples 84-91, wherein the plurality of actuators comprise threaded rods having external threads.

Example 93. The prosthetic heart valve of any example herein, particularly example 92, wherein for each pair of proximal and distal frame members that have an actuator extending therethrough, the proximal frame member has a non-threaded bore, the distal frame member has a bore with internal threads, and the actuator extends through the non-threaded bore of the proximal frame member and the bore of the distal frame member, wherein the external threads of the actuator engage the internal threads of the distal frame member.

Example 94. The prosthetic heart valve of any example herein, particularly example 93, wherein for each pair of proximal and distal frame members that have an actuator extending therethrough, the distal frame member includes a cut-out region and a nut disposed in the cut-out region, wherein the nut defines the internal threads of the bore of the distal member.

Example 95. The prosthetic heart valve of any example herein, particularly any one of examples 84-94, wherein each post includes a cantilevered extension portion that extends toward an inflow end of the frame.

Example 96. The prosthetic heart valve of any example herein, particularly example 95, further comprising an inner skirt and/or an outer skirt mounted on the frame, wherein the inner skirt and/or the outer skirt are secured to the extension portions with sutures.

Example 97. The prosthetic heart valve of any example herein, particularly any one of examples 95-96, wherein cusp edge portions of leaflets of the valvular structure are secured to the extension portions with sutures.

Example 98. A prosthetic heart valve comprising:
a radially expandable and compressible frame comprising:
a plurality of pairs of axially extending frame members, wherein each pair of frame members includes a first frame member and a second frame member axially spaced from the first frame member, wherein the pairs of frame members are circumferentially spaced from each other around a circumference of the frame, wherein the first frame member of each pair includes a cut-out region housing a nut having internal threads;
a plurality of threaded rods extending through respective pairs of first and second frame members, wherein each threaded rod includes external threads that engage the internal threads of a corresponding nut, wherein rotation of the threaded rods in a first direction produces radial expansion of the frame from a radially compressed state to a radially expanded state;
a valvular structure disposed within the frame and configured to regulate the flow of blood through the frame in one direction.

Example 99. The prosthetic heart valve of any example herein, particularly example 98, wherein the frame further comprises a plurality of axially extending posts and a plurality of connecting struts, wherein each post is circumferentially disposed between a first and a second pair of frame members and the connecting struts couple the posts to the pairs of frame members.

Example 100. The prosthetic heart valve of any example herein, particularly example 99, wherein each post is connected to (i) an adjacent first frame member of a first adjacent pair of frame members by two connecting struts, (ii) an adjacent second frame member of the first adjacent pair by two connecting struts, (iii) an adjacent first frame member of a second adjacent pair of frame members by two connecting struts, and (iv) an adjacent second frame member of the second adjacent pair by two connecting struts.

Example 101. The prosthetic heart valve of any example herein, particularly any one of examples 99-100, wherein each connecting strut has a concave curved portion and a convex curved portion separated by an inflection point.

Example 102. The prosthetic heart valve of any example herein, particularly any one of examples 99-101, wherein the struts, the posts, and the first and second frame members are arranged to form a plurality of hexagonal cells and a plurality of diamond-shaped cells, wherein each diamond-shaped cell disposed within one of the hexagonal cells.

Example 103. The prosthetic heart valve of any example herein, particularly example 102, wherein each diamond-shaped cell is centered within a respective hexagonal cell.

Example 104. The prosthetic heart valve of any example herein, particularly any one of examples 102-103, wherein each hexagonal cell defines an inflow apex of the frame and an outflow apex of the frame.

Example 105. The prosthetic heart valve of any example herein, particularly any one of examples 102-104, wherein there are exactly six hexagonal cells and exactly six diamond-shaped cells.

Example 106. The prosthetic heart valve of any example herein, particularly any one of examples 102-105, wherein the hexagonal cells extend the entire length of the frame.

Example 107. The prosthetic heart valve of any example herein, particularly any one of examples 98-106, wherein the valvular structure comprises a plurality of leaflets, each leaflet comprising two commissure tabs on opposite sides of the leaflet, wherein each commissure tab is paired with an adjacent commissure tab of an adjacent leaflet to form a commissure, wherein each commissure is secured to an adjacent post.

Example 108. The prosthetic heart valve of any example herein, particularly example 107, wherein each post that is adjacent a commissure comprises a slot and a pair of commissure tabs of the adjacent commissure extends through the slot.

In view of the many possible examples to which the principles of the disclosure may be applied, it should be recognized that the illustrated examples are only preferred examples and should not be taken as limiting the scope. Rather, the scope is defined by the following claims. We therefore claim all that comes within the scope and spirit of these claims.

The invention claimed is:

1. A delivery apparatus, comprising:
a handle,
one or more actuator assemblies extending from the handle, each actuator assembly comprising:
a first actuation member having a distal end portion configured to abut an outflow end portion of a prosthetic heart valve, the distal end portion comprising first and second support extensions; and
a second actuation member extending through the first actuation member and having a distal end portion configured to releasably couple an actuator of the prosthetic heart valve;
wherein rotation of the second actuation member in a first direction radially expands the prosthetic valve and rotation of the second actuation member in a second direction radially compresses the prosthetic valve; and
wherein the first support extension is configured to extend partially over a radial inner surface of the prosthetic valve and the second support extension is configured to extend partially over a radial outer surface of the prosthetic valve to inhibit rotation of the prosthetic valve relative to the actuator assemblies.

2. The delivery apparatus of claim 1, wherein the second actuation member comprises a central protrusion.

3. The delivery apparatus of claim 2, wherein the central protrusion is sized such that it does not contact an inner surface of the first actuation member.

4. The delivery apparatus of claim 1, wherein the distal end portion of the second actuation member comprises one or more flexible elongated elements.

5. The delivery apparatus of claim 4, wherein each elongated element comprises a protrusion extending radially inwardly toward a longitudinal axis of the second actuation member.

6. The delivery apparatus of claim 5, wherein the one or more elongated elements bias radially outwardly from a longitudinal axis of the second actuation member.

7. The delivery apparatus of claim 1, wherein the distal end portion of the second actuation member comprises a driver head having an engagement member extending distally from the driver head.

8. The delivery apparatus of claim 7, wherein the engagement member comprises a square shape with chamfered corners in cross-section.

9. The delivery apparatus of claim 7, wherein the engagement member is configured to selectively extend into a corresponding recess on the actuator of the prosthetic heart valve.

10. The delivery apparatus of claim 7, wherein the distal end portion of the second actuation member further comprises a gripper member comprising one or more arms configured to releasably couple the actuator of the prosthetic valve.

11. The delivery apparatus of claim 10, wherein the one or more arms comprise a plurality of arms.

12. The delivery apparatus of claim 10, wherein the one or more arms are movable between an expanded position and a compressed position.

13. The delivery apparatus of claim 10, wherein the one or more arms bias radially outwardly from a longitudinal axis of the second actuation member.

14. The delivery apparatus of claim 10, wherein each arm comprises an opening configured to selectively couple a respective projection of the actuator.

15. The delivery apparatus of claim 1, wherein rotation of the second actuation member in a second direction is configured to cause corresponding rotation of a corresponding actuator to radially compress the prosthetic valve.

16. An assembly, comprising:
a prosthetic heart valve comprising:
a radially expandable and compressible frame having an inflow end portion and an outflow end portion, the frame comprising a plurality of actuation mechanisms, each actuation mechanism comprising:
a first frame member having a first inner bore and a second frame member having a second inner bore, the first and second frame members being spaced apart axially from one another, and
a rod having an external threaded surface and extending through the first and second inner bores; and
a delivery apparatus comprising:
a handle,
one or more actuator assemblies extending from the handle, each actuator assembly comprising:
a first actuation member having a distal end portion abutting the outflow end portion of the frame, and
a second actuation member extending through the first actuation member, the second actuation member comprising a distal end portion coupled to the rod;
wherein rotation of the second actuation member in a first direction causes corresponding rotation of the rod such that the first and second frame members move axially toward one another to expand the prosthetic valve; and
wherein the first actuation member further comprises first and second support extensions configured to inhibit rotation of the frame relative to the first actuation member during expansion of the frame.

17. The assembly of claim 16, wherein the first support extension extends partially over a radial inner surface of the frame and the second support extension extends partially over a radial outer surface of the frame.

18. The assembly of claim 16, wherein rotation of the second actuation member in a second direction causes corresponding rotation of the rod such that the first and second frame members move axially away from one another to radially compress the prosthetic valve.

19. The assembly of claim 16, each rod comprising a stopper disposed between the first and second frame members, the stopper configured to selectively abut an inflow end portion of the second frame member to prevent over crimping of the frame.

* * * * *